United States Patent
Patterson et al.

(10) Patent No.: US 11,286,443 B2
(45) Date of Patent: Mar. 29, 2022

(54) DETERGENT COMPOSITIONS COMPRISING LIPASES

(71) Applicant: The Procter & Gamble Company, Cincinnati, OH (US)

(72) Inventors: Steven George Patterson, Tyne & Wear (GB); Nazarmohammad Gulamhussain Momin, Newcastle upon Tyne (GB); Miguel D. G. P. Toscano, Frederiksberg (DK); Thomas A. Poulsen, Ballerup (DK); Carsten H. Hansen, Vaerloese (DK); Lone Baunsgaard, Vaerloe (DK); Keith Gibson, Bagsvaerd (DK)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/140,857

(22) Filed: Sep. 25, 2018

(65) Prior Publication Data
US 2019/0093054 A1    Mar. 28, 2019

(30) Foreign Application Priority Data

Sep. 27, 2017 (EP) .................................... 17193475
Jun. 28, 2018 (EP) .................................... 18180593

(51) Int. Cl.
| | |
|---|---|
| *C11D 3/386* | (2006.01) |
| *C11D 17/04* | (2006.01) |
| *C11D 3/22* | (2006.01) |
| *C11D 17/00* | (2006.01) |
| *C12N 9/20* | (2006.01) |

(52) U.S. Cl.
CPC .......... *C11D 3/38627* (2013.01); *C11D 3/222* (2013.01); *C11D 17/0039* (2013.01); *C11D 17/043* (2013.01); *C11D 17/045* (2013.01); *C12N 9/20* (2013.01); *C12Y 301/01003* (2013.01); *C12Y 301/0105* (2013.01); *C12Y 301/01013* (2013.01); *C12Y 301/01074* (2013.01)

(58) Field of Classification Search
None
See application file for complete search history.

(56) References Cited

U.S. PATENT DOCUMENTS

| | | | |
|---|---|---|---|
| 2010/0034797 A1* | 2/2010 | Svendsen ................ | A61P 43/00 424/94.2 |
| 2016/0068787 A1 | 3/2016 | Casella | |
| 2016/0075976 A1* | 3/2016 | Andersen ................ | C11D 3/386 435/264 |
| 2016/0076012 A1 | 3/2016 | Malten et al. | |
| 2017/0152467 A1 | 6/2017 | Lant et al. | |

FOREIGN PATENT DOCUMENTS

| | | |
|---|---|---|
| JP | 2016506237 A | 3/2016 |
| WO | 2014186464 A1 | 11/2014 |
| WO | WO2017005640 A1 | 1/2017 |
| WO | 2017091364 A1 | 6/2017 |

OTHER PUBLICATIONS

Search Report for appl. 18196702.7-1105, dated Feb. 6, 2019, 22 pages.
Search Report for application 17193475.5-1105, dated Jun. 18, 2018, 19 pages.
Extended European Search Report and Search Opinion; Application No. 17193475.5; dated Mar. 15, 2018; 21 pages.
Extended European Search Report and Search Opinion; Application No. 18196702.7; dated May 15, 2019; 20 pages.
International Search Report and Written Opinion; Application Ser. No. PCT/US2018/052543; dated Feb. 11, 2019, 27 pages.

* cited by examiner

*Primary Examiner* — Paul J Holland
(74) *Attorney, Agent, or Firm* — Carrie Schwartz

(57) ABSTRACT

Detergent compositions that include a lipase variant of a parent lipase which has lipase activity and includes one or more substitutions corresponding to G23S, D27N, A40, F51I,L, E56R, D57N, V60E,K, K98I, N101D, R118, G163S, T231R, N233R, Y220F, T244E, and P256T using SEQ ID NO: 2 for numbering. Water-soluble unit dose articles including water-soluble film and a detergent composition including lipase variants. Methods of cleaning and/or treatment of surfaces using such compositions.

12 Claims, 1 Drawing Sheet
Specification includes a Sequence Listing.

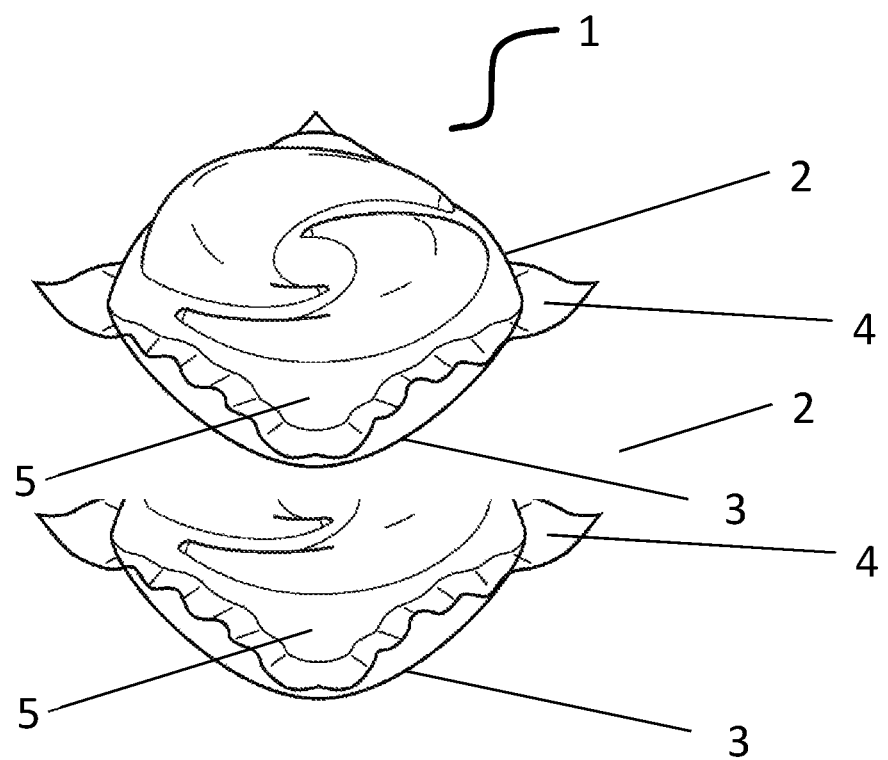

SEQUENCE LISTING

```
<160> NUMBER OF SEQ ID NOS: 2

<210> SEQ ID NO 1
<211> LENGTH: 807
<212> TYPE: DNA
<213> ORGANISM: Thermomyces lanuginosus
<220> FEATURE:
<221> NAME/KEY: CDS
<222> LOCATION: (1)..(807)
<220> FEATURE:
<221> NAME/KEY: mat_peptide
<222> LOCATION: (1)..()

<400> SEQUENCE: 1 gag gtc tcg cag gat ctg ttt aac cag ttc aat ctc ttt gca cag tat        48
Glu Val Ser Gln Asp Leu Phe Asn Gln Phe Asn Leu Phe Ala Gln Tyr
1               5                   10                  15 tct gca gcc gca tac tgc gga aaa aac aat gat gcc cca gct ggt aca        96
Ser Ala Ala Ala Tyr Cys Gly Lys Asn Asn Asp Ala Pro Ala Gly Thr
                20                  25                  30 aac att acg tgc acg gga aat gcc tgc ccc gag gta gag aag gcg gat       144
Asn Ile Thr Cys Thr Gly Asn Ala Cys Pro Glu Val Glu Lys Ala Asp
            35                  40                  45 gca acg ttt ctc tac tcg ttt gaa gac tct gga gtg ggc gat gtc acc       192
Ala Thr Phe Leu Tyr Ser Phe Glu Asp Ser Gly Val Gly Asp Val Thr
        50                  55                  60 ggc ttc ctt gct ctc gac aac acg aac aaa ttg atc gtc ctc tct ttc       240
Gly Phe Leu Ala Leu Asp Asn Thr Asn Lys Leu Ile Val Leu Ser Phe
65                  70                  75                  80 cgt ggc tct cgt tcc ata gag aac tgg atc ggg aat ctt aac ttc gac       288
Arg Gly Ser Arg Ser Ile Glu Asn Trp Ile Gly Asn Leu Asn Phe Asp
                85                  90                  95 ttg aaa gaa ata aat gac att tgc tcc ggc tgc agg gga cat gac ggc       336
Leu Lys Glu Ile Asn Asp Ile Cys Ser Gly Cys Arg Gly His Asp Gly
                100                 105                 110 ttc act tcg tcc tgg agg tct gta gcc gat acg tta agg cag aag gtg       384
Phe Thr Ser Ser Trp Arg Ser Val Ala Asp Thr Leu Arg Gln Lys Val
            115                 120                 125 gag gat gct gtg agg gag cat ccc gac tat cgc gtg gtg ttt acc gga       432
Glu Asp Ala Val Arg Glu His Pro Asp Tyr Arg Val Val Phe Thr Gly
        130                 135                 140 cat agc ttg ggt ggt gca ttg gca act gtt gcc gga gca gac ctg cgt       480
His Ser Leu Gly Gly Ala Leu Ala Thr Val Ala Gly Ala Asp Leu Arg
145                 150                 155                 160 gga aat ggg tat gat atc gac gtg ttt tca tat ggc gcc ccc cga gtc       528
Gly Asn Gly Tyr Asp Ile Asp Val Phe Ser Tyr Gly Ala Pro Arg Val
                165                 170                 175 gga aac agg gct ttt gca gaa ttc ctg acc gta cag acc ggc gga aca       576
Gly Asn Arg Ala Phe Ala Glu Phe Leu Thr Val Gln Thr Gly Gly Thr
                180                 185                 190 ctc tac cgc att acc cac acc aat gat att gtc cct aga ctc ccg ccg       624
Leu Tyr Arg Ile Thr His Thr Asn Asp Ile Val Pro Arg Leu Pro Pro
            195                 200                 205 cgc gaa ttc ggt tac agc cat tct agc cca gag tac tgg atc aaa tct       672
Arg Glu Phe Gly Tyr Ser His Ser Ser Pro Glu Tyr Trp Ile Lys Ser
        210                 215                 220
```

| | | | | | | | | | | | | |
|---|---|---|---|---|---|---|---|---|---|---|---|---|
| gga | acc | ctt | gtc | ccc | gtc | acc | cga | aac | gat | atc | gtg | aag | ata | gaa | ggc | 720 |
| Gly | Thr | Leu | Val | Pro | Val | Thr | Arg | Asn | Asp | Ile | Val | Lys | Ile | Glu | Gly |
| 225 | | | | 230 | | | | | 235 | | | | | 240 | | |

| | | | | | | | | | | | | |
|---|---|---|---|---|---|---|---|---|---|---|---|---|
| atc | gat | gcc | acc | ggc | ggc | aat | aac | cag | cct | aac | att | ccg | gat | atc | cct | 768 |
| Ile | Asp | Ala | Thr | Gly | Gly | Asn | Asn | Gln | Pro | Asn | Ile | Pro | Asp | Ile | Pro |
| | | | | 245 | | | | | 250 | | | | | 255 | | |

| | | | | | | | | | |
|---|---|---|---|---|---|---|---|---|---|
| gcg | cac | cta | tgg | tac | ttc | ggg | tta | att | ggg | aca | tgt | ctt | | | | 807 |
| Ala | His | Leu | Trp | Tyr | Phe | Gly | Leu | Ile | Gly | Thr | Cys | Leu |
| | | 260 | | | | | 265 | | | | | |

<210> SEQ ID NO 2
<211> LENGTH: 269
<212> TYPE: PRT
<213> ORGANISM: Thermomyces lanuginosus

<400> SEQUENCE: 2

Glu Val Ser Gln Asp Leu Phe Asn Gln Phe Asn Leu Phe Ala Gln Tyr
1               5                   10                  15

Ser Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60

Gly Phe Leu Ala Leu Asp Asn Thr Asn Lys Leu Ile Val Leu Ser Phe
65                  70                  75                  80

Arg Gly Ser Arg Ser Ile Glu Asn Trp Ile Gly Asn Leu Asn Phe Asp
                85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
    130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
    210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265

DETERGENT COMPOSITIONS COMPRISING LIPASES

REFERENCE TO A SEQUENCE LISTING

This application contains a Sequence Listing in computer readable form, which is incorporated herein by reference.

FIELD OF THE INVENTION

This invention relates to detergent compositions and water-soluble unit dose articles comprising detergent compositions, comprising lipase enzymes, as well as methods of making and using such compositions. The invention also relates to liquid products, detergent compositions and water-soluble unit dose articles comprising detergent compositions in which the lipase variant is encapsulated in a microcapsule. Such compositions and articles are preferably fabric and home care products, most preferably for laundry.

BACKGROUND OF THE INVENTION

Detergent manufacturers continue to try to provide cleaning compositions, particularly fabric and dish-cleaning compositions which provide the most robust cleaning systems. Lipases are important biocatalysts which have shown to be very useful in detergent compositions contributing to the removal of oily soils and stains by hydrolyzing triglycerides to generate fatty acids. Following hydrolysis the hydrolysed soils are more easily removed from fabric surfaces in the wash process in the presence of other detergent components. Many known lipases provide good wash performance, however, they may also be prone to forming odor-generating short-chain fatty acids during wash and/or have short storage stability.

Stability can be particularly problematic for example when in contact with incompatible components of a detergent composition or on exposure to significantly higher or lower temperatures than ambient temperature either during storage or during a wash or treatment step. If stability is not sufficiently robust, this leads to loss of activity or efficacy of the composition as a whole, and in particular to loss of enzyme activity. Wild-type *Thermomyces lanuginosus* lipase (synonym *Humicola lanuginosa*) sold under the tradename LIPOLASE™ and variants thereof have been commercialized as active ingredients in detergent compositions for the removal of lipid stains by hydrolyzing triglycerides to generate fatty acids. However, there is still a need for compositions comprising lipases which provide good wash performance, reduced odor-generation and/or improved storage stability/longer shelf life/increased thermostability.

SUMMARY OF THE INVENTION

The present invention relates to a detergent composition comprising a variant of a parent lipase which variant has lipase activity, said variant having at least 60%, but less than 100% sequence identity with SEQ ID NO: 2 and comprising (i) one or more substitutions at positions corresponding to position 40, 118, T244E and V60E; and (ii) one or more substitutions at positions corresponding to T231R and N233R. Preferably the lipase variant comprises substitutions at positions corresponding to both positions 40 and 118, more preferably one or more substitutions at positions corresponding to A40I and R118F.

The present invention also relates to a detergent composition comprising a variant of a parent lipase which variant has lipase activity, said variant having at least 60%, but less than 100% sequence identity with SEQ ID NO: 2 and comprising one or more substitutions at positions corresponding to G23S, D27N, A40I, F51I,L, E56R, D57N, V60E,K, K98I, N101D, R118F, G163S, T231R, N233R, Y220F, T244E, and P256T; and a detergent adjunct. Preferably the detergent composition is in the form of a liquid, preferably comprising less than 20 wt % water.

In a further aspect the invention also relates to (i) one or more substitutions at positions corresponding to position 23, 51 and 56, preferably one or more substitutions at positions corresponding to G23S, F51I and E56R; and (ii) one or more substitutions at positions corresponding to T231R and N233R.

The invention also provides a water-soluble unit dose article comprising a water-soluble film and the detergent composition comprising: the lipase variant; and a detergent adjunct. The lipase variant may be present in the water-soluble unit dose article in a liquid composition or in a solid composition. Preferably the detergent composition comprising the lipase variant is a liquid composition.

This invention also relates to a method of making a detergent composition comprising the lipase variant the method comprising a first step of mixing a detergent adjunct and a lipase variant to form a detergent composition. Preferably the detergent composition is then formed into a unit dose form, optionally by encasing the detergent composition in a film, preferably a water-soluble film. The lipase variant is preferably present in the detergent composition herein in a composition comprising less than 20 wt % water. The water-soluble unit dose article may comprise one compartment or more than one compartment. The water-soluble unit dose article comprises the lipase variant in one or more compartments, most preferably in one compartment of a multi-compartment unit dose detergent.

This invention also relates to a process for washing fabric comprising the steps of:
(i) forming an aqueous wash liquor comprising water and the detergent composition described herein;
(ii) (ii) treating the surface with the aqueous wash liquor, preferably at a temperature of 60° C. or less, or preferably below 40° C. or less, or preferably 30° C. or less; and
(iii) (iii) rinsing the surface. In a preferred method the water-soluble unit dose article according to the invention is combined with sufficient water to dissolve the water-soluble film and dilute the laundry detergent composition, preferably by a factor of between 300 and 3000 fold, forming the aqueous wash liquor.

Preferably the lipase variant has at least 60%, but less than 100% sequence identity with SEQ ID NO: 2 and comprises one or more substitutions at positions corresponding to G23S, D27N, A40I, F51I,L, E56R, D57N, V60E,K, K98I, N101D, R118F, G163S, Y220F, T244E, and P256T. Preferably the variant additionally comprises one or both substitutions at positions corresponding to T231R and/or N233R.

A preferred variant comprises a substitution at a position corresponding to F51I,L. A preferred variant comprises a substitution at a position corresponding to E56R. A preferred variant comprises a substitution at a position corresponding to R118F. A preferred variant comprises one or more substitutions at positions corresponding to F51I,L, E56R and/or R118F. A preferred variant comprises a substitution at a position corresponding to P256T. A preferred variant comprises a substitution at a position corresponding to D27N. A preferred variant comprises a substitution at a position corresponding to G23S. A preferred variant comprises a substitution at a position corresponding to T244E. A preferred variant comprises a substitution at a position corresponding to A40I. A preferred variant comprises a substitution at a position corresponding to K98I. A preferred variant comprises a substitution at a position corresponding to D57N. A preferred variant comprises a substitution at a position corresponding to Y220F. A preferred variant comprises a substitution at a position corresponding to G163S.

In one aspect the invention relates to a detergent composition comprising a lipase enzyme, preferably the lipase variant, encapsulated in a microcapsule. According to one preferred aspect the membrane of the microcapsule is produced by cross-linking of a polybranched polyamine having a molecular weight of more than 1 kDa. In a further aspect the detergent composition comprises a microcapsule composition, comprising a lipase variant of the invention, preferably entrapped in a compartment formed by a membrane, which membrane is produced by cross-linking of (a) a polybranched polyamine having a molecular weight of more than 800 Da, and (b) an aliphatic or aromatic amine having a molecular weight of less than 300 Da; wherein the weight ratio of (a)/(b) is in the range of 0.1 to 1000.

Lipase: The terms "lipase", "lipase enzyme", "lipolytic enzyme", "lipid esterase", "lipolytic polypeptide", and "lipolytic protein" refers to an enzyme in class EC3.1.1 as defined by Enzyme Nomenclature. It may have lipase activity (triacylglycerol lipase, EC3.1.1.3), cutinase activity (EC3.1.1.74), sterol esterase activity (EC3.1.1.13) and/or wax-ester hydrolase activity (EC3.1.1.50). For purposes of the present invention, lipase activity is determined according to the procedure described in the Examples. In one aspect, the variants of the present invention have at least 20%, e.g., at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or 100% of the lipase activity of the polypeptide of SEQ ID NO: 2.

In one aspect, the invention relates to water-soluble unit dose article comprising a water-soluble film and the detergent composition comprising the lipase variant and a detergent adjunct comprising microcapsule compositions, wherein the membrane of the microcapsule is produced by cross-linking of a polybranched polyamine having a molecular weight of more than 1 kDa, wherein the microcapsule comprising a lipase variant of the invention.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a variant. The boundaries of the coding sequence are generally determined by an open reading frame, which begins with a start codon such as ATG, GTG or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a variant of the present invention. Each control sequence may be native (i.e., from the same gene) or foreign (i.e., from a different gene) to the polynucleotide encoding the variant or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a variant.

Detergent Adjunct: means any liquid, solid or gaseous material selected for the particular type of detergent composition desired and the form of the product (e.g., liquid, granule, powder, bar, paste, spray, tablet, gel, or foam composition).

Detergent composition: The terms "detergent composition" and "detergent formulation" are used in reference to mixtures which are intended for use in a wash process for the cleaning of soiled objects. The term is used particularly in reference to laundering fabrics and/or garments (e.g., "laundry detergents"). Unless otherwise indicated, these may include granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, as well as cleaning auxiliaries such as bleach additives and "stain-stick" or pre-treat types. In alternative aspects, the term refers to other detergents, such as those used to clean dishes, cutlery, etc. (e.g., "dishwashing detergents"). The term "detergent composition" is not intended to be limited to compositions that contain surfactants. It is intended that in addition to the variants essential to the invention, the term encompasses detergents that may contain any detergent adjunct, e.g., surfactants, builders, chelators or chelating agents, bleach system or bleach components, polymers, fabric conditioners, foam boosters, suds suppressors, dyes, perfume, tarnish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, solubilizers and solvents. Detergent compositions may also be used for fabric treatment either in a wash step or in a fabric treatment step, for example they may provide fabric freshening, fabric softening and/or colour-rejuvenation step. The detergent compositions herein are particularly comprised in a water-soluble unit dose article.

Expression: The term "expression" includes any step involved in the production of a variant including, but not limited to, transcription, post-transcriptional modification, translation, post-translational modification, and secretion.

Expression vector: The term "expression vector" means a linear or circular DNA molecule that comprises a polynucleotide encoding a variant and is operably linked to control sequences that provide for its expression.

Fragment: The term "fragment" means a polypeptide having one or more (e.g., several) amino acids absent from the amino and/or carboxyl terminus of a polypeptide; wherein the fragment has lipase activity. In one aspect, a fragment contains at least 50%, at least 55%, at least 60%, at least 65%, at least 70%, at least 75%, at least 80%, at least 85%, at least 90%, or at least 95% but less than 100% of the number of amino acids 1 to 269 of SEQ ID NO: 2.

High stringency conditions: The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent lipase. Such improved properties include, but are not limited to, detergent stability, stability in detergent with protease present, protease stability, chemical stability, oxidation stability, pH stability, stability under storage conditions, and thermostability.

Isolated: The term "isolated" means a substance in a form or environment which does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Low stringency conditions: The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 269 of SEQ ID NO: 2. It is known in the art that a host cell may produce a mixture of two or more different mature polypeptides (i.e., with a different C-terminal and/or N-terminal amino acid) expressed by the same polynucleotide.

Mature polypeptide coding sequence: The term "mature polypeptide coding sequence" means a polynucleotide that encodes a mature polypeptide having lipase activity. In one aspect, the mature polypeptide coding sequence is nucleotides 1 to 807 of SEQ ID NO: 1.

Medium stringency conditions: The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

Medium-high stringency conditions: The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent or parent lipase: The term "parent" or "parent lipase" means a lipase to which an alteration is made to produce the enzyme variants of the present invention. The parent lipase may be a naturally occurring (wild-type) polypeptide or a variant or fragment thereof.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

$$\text{(Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the –nobrief option) is used as the percent identity and is calculated as follows:

(Identical Deoxyribonucleotides×100)/(Length of Alignment−Total Number of Gaps in Alignment).

Stability: The stability of a lipase variant of the invention may be expressed as the residual activity or the residual performance of said lipase during or after exposure to various test conditions such as e.g. storage in a detergent composition, at various temperatures, at various pH, in the presence of different components such as protease, chemicals, and/or oxidative substances (stress conditions) or during use in a wash process. The stability of a lipase variant can be measured relative to a known activity or performance of a parent lipase, e.g., the lipase shown as SEQ ID NO: 2, or alternatively to a known activity or performance of the lipase variant when initially added to a detergent composition optionally stored cold or frozen or relative to the lipase variant stored cold or frozen (unstressed conditions).

Subsequence: The term "subsequence" means a polynucleotide having one or more (e.g., several) nucleotides absent from the 5' and/or 3' end of a mature polypeptide coding sequence; wherein the subsequence encodes a fragment having lipase activity. In one aspect, a subsequence contains at least 50%, at least 55%, at least 60%, at least 65%, at least 70%, at least 75%, at least 80%, at least 85%, at least 90%, or at least 95% but less than 100% of the number of nucleotides 1 to 807 of SEQ ID NO: 1.

Variant: The term "variant" means a polypeptide having lipase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position. The variants of the present invention have at least 20%, e.g., at least 40%, at least 50%, at least 60%, at least 70%, at least 80%, at least 90%, at least 95%, or at least 100% of the lipase activity of the polypeptide of SEQ ID NO: 2.

Very high stringency conditions: The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Very low stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

Wild-type lipase: The term "wild-type" lipase means a lipase expressed by a naturally occurring microorganism, such as a bacterium, yeast, or filamentous fungus found in nature.

Conventions for Designation of Variants

For purposes of the present invention, the polypeptide disclosed as SEQ ID NO: 2 is used to determine the corresponding amino acid residue in another lipase. The amino acid sequence of another lipase is aligned with SEQ ID NO: 2, and based on the alignment, the amino acid position number corresponding to any amino acid residue in the polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another lipase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26:_1899-1900), and EMBOSS EMMA employing ClustalW (1.83 or later; Thompson et al., 1994, *Nucleic Acids Research* 22: 4673-4680), using their respective default parameters.

When the other enzyme has diverged from the polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions. For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions. For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA".

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Multiple Alterations.

Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different alterations. Where different alterations can be introduced at a position, the different alterations are separated by a comma, e.g., "Arg170Tyr,Glu" or "R170Y,E" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg170Ala".

BRIEF DESCRIPTION OF THE DRAWINGS

FIG. 1 is a water-soluble unit dose article according to the present invention.

DETAILED DESCRIPTION OF THE INVENTION

FIG. 1 discloses a water-soluble unit dose article (1) according to the present invention. The water-soluble unit dose article (1) comprises a first water-soluble film (2) and a second water-soluble film (3) which are sealed together at a seal region (4). The laundry detergent composition (5) is comprised within the water-soluble soluble unit dose article (1).

Disclosed are compositions comprising variants of a parent lipase which variants have lipase activity, has at least 60%, but less than 100% sequence identity with SEQ ID NO: 2, e.g., derived from *Thermomyces lanuginosus*.

Variants

The present invention provides a detergent composition and a water-soluble unit dose article comprising a detergent composition, comprising a variant of a parent lipase which variant has lipase activity, has at least 60%, but less than 100% sequence identity with SEQ ID NO: 2 and comprises one or more (e.g. several) substitutions at positions corresponding to G23S, D27N, A40I, F51I,L, E56R, D57N, V60E,K, K98I, N101D, R118F, G163S, T231R, N233R, Y220F, T244E, and P256T.

Preferably the lipase variant has at least 60%, but less than 100% sequence identity with SEQ ID NO: 2 and comprises one or more substitutions at positions corresponding to G23S, D27N, A40I, F51I,L, E56R, D57N, E, and P256T. Preferably the variant additionally comprises one or both substitutions at positions corresponding to T231R and/or N233R.

A preferred variant comprises a substitution at a position corresponding to G23S. A preferred variant comprises a substitution at a position corresponding to D27N. A preferred variant comprises a substitution at a position corresponding to A40I. A preferred variant comprises a substitution at a position corresponding to F51I,L. A preferred variant comprises a substitution at a position corresponding to E56R. A preferred variant comprises a substitution at a position corresponding to D57N. A preferred variant comprises a substitution at a position corresponding to V60E,K. A preferred variant comprises a substitution at a position corresponding to K98I. A preferred variant comprises a substitution at a position corresponding to N101D. A preferred variant comprises a substitution at a position corresponding to R118F. A preferred variant comprises a substitution at a position corresponding to G163S. A preferred variant comprises a substitution at a position corresponding to Y220F. A preferred variant comprises a substitution at a position corresponding to T244E. A preferred variant comprises a substitution at a position corresponding to P256T.

A preferred variant comprises one or more substitutions at positions corresponding to F51I,L, E56R and/or R118F.

In preferred embodiment, a variant of the invention comprises any one of the following set of substitutions:

G23S + T231R + N233R
D27N + T231R + N233R
A40I + T231R + N233R
F51I + T231R + N233R
F51L + T231R + N233R
E56R + T231R + N233R
D57N + T231R + N233R
V60E + T231R + N233R
V60K + T231R + N233R
K98I + T231R + N233R
N101D + T231R + N233R
R118F + T231R + N233R
G163S + T231R + N233R
Y220F + T231R + N233R
T231R + N233R + T244E
T231R + N233R + P256T

In an embodiment the variant comprises substitutions at positions corresponding to T231R+N233R and one or more (e.g., several) substitutions at positions corresponding to G23S, D27N, A40I, F51I,L, E56R, D57N, V60E,K, K98I, N101D, R118F, G163S, Y220F, T244E, and P256T.

In a preferred embodiment the variant comprises substitutions corresponding to E56R+T231R+N233R and one or more (e.g., several) substitutions at positions corresponding to G23S, D27N, A40I, F51I,L, D57N, V60E,K, K98I, N101D, R118F, G163S, Y220F, T244E, and P256T.

In a preferred embodiment the variant comprises substitutions at positions corresponding to R118F+T231R+N233R and one or more (e.g., several) substitutions at positions corresponding to G23S, D27N, A40I, F51I,L, E56R, D57N, V60E,K, K98I, N101D, G163S, Y220F, T244E, and P256T.

In a more preferred embodiment variant comprises substitutions at positions corresponding to E56R+R118F+T231R+N233R and one or more (e.g., several) substitutions at positions corresponding to G23S, D27N, A40I, F51I,L, D57N, V60E,K, K98I, N101D, G163S, Y220F, T244E, and P256T.

In an even more preferred embodiment the variant comprises substitutions at positions corresponding to E56R+R118F+T231R+N233R+P256T and one or more (e.g., several) substitutions at positions corresponding to G23S, D27N, A40I, F51I,L, D57N, V60E,K, K98I, N101D, G163S, Y220F, and T244E.

In an even more preferred embodiment the variant comprises substitutions at positions corresponding to F51I,L+E56R+R118F+T231R+N233R and one or more (e.g., several) substitutions at positions corresponding to G23S, D27N, A40I, D57N, V60E,K, K98I, N101D, G163S, Y220F, T244E and P256T.

In an even more preferred embodiment the variant comprises substitutions at positions corresponding to F51I,L+E56R+R118F+T231R+N233R+P256T and one or more (e.g., several) substitutions at positions corresponding to G23S, D27N, A40I, D57N, V60E,K, K98I, N101D, G163S, Y220F, and T244E.

In another more preferred embodiment the variant comprises substitutions at positions corresponding to G23S+F51I,L+E56R+R118F+T231R+N233R and one or more (e.g., several) substitutions at positions corresponding to D27N, A40I, D57N, V60E,K, K98I, N101D, G163S, Y220F, T244E, and P256T.

In another more preferred embodiment the variant comprises substitutions at positions corresponding to G23S+F51I,L+E56R+R118F+T231R+N233R+P256T and one or more (e.g., several) substitutions at positions corresponding to D27N, A40I, D57N, V60E,K, K98I, N101D, G163S, Y220F, and T244E.

In a further even more preferred embodiment the variant comprises substitutions at positions corresponding to D27N+F51I,L+E56R+R118F+T231R+N233R+P256T and one or more (e.g., several) substitutions at positions corresponding to G23S, A40I, D57N, V60E,K, K98I, N101D, G163S, Y220F, and T244E.

In an additional even more preferred embodiment variant comprises substitutions at positions corresponding to A40I+F51I,L+E56R+R118F+T231R+N233R and one or more (e.g., several) substitutions at positions corresponding to G23S, D27N, D57N, V60E,K, K98I, N101D, G163S, Y220F, T244E and P256T.

In a further even more preferred embodiment the variant comprises substitutions at positions corresponding to D27N+F51I,L+E56R+R118F+T231R+N233R and one or more (e.g., several) substitutions at positions corresponding to G23S, A40I, D57N, V60E,K, K98I, N101D, G163S, Y220F, T244E and P256T.

In a further even more preferred embodiment the variant comprises substitutions at positions corresponding to D27N+F51I,L+E56R+R118F+T231R+N233R+P256T and one or more (e.g., several) substitutions at positions corresponding to G23S, A40I, D57N, V60E,K, K98I, N101D, G163S, Y220F, and T244E.

In an additional even more preferred embodiment variant comprises substitutions at positions corresponding to A40I+F51I,L+E56R+R118F+T231R+N233R+P256T and one or more (e.g., several) substitutions at positions corresponding to G23S, D27N, D57N, V60E,K, K98I, N101D, G163S, Y220F, and T244E.

In a further even more preferred embodiment the variant comprises substitutions at positions corresponding to F51I,L+E56R+D57N+R118F+T231R+N233R+P256T and one or more (e.g., several) substitutions at positions corresponding to G23S, D27N, A40I, V60E,K, K98I, N101D, G163S, Y220F, and T244E.

In a further preferred embodiments the variant comprises substitutions at positions corresponding to F51I,L+E56R+D57N+K98I+R118F+T231R+N233R and one or more (e.g., several) substitutions at positions corresponding to G23S, D27N, A40I, V60E,K, N101D, G163S, Y220F, T244E and P256T.

In a further preferred embodiments the variant comprises substitutions at positions corresponding to F51I,L+E56R+D57N+K98I+R118F+T231R+N233R+P256T and one or more (e.g., several) substitutions at positions corresponding to G23S, D27N, A40I, V60E,K, N101D, G163S, Y220F, and T244E.

In a further more preferred embodiment the variant comprises substitutions at positions corresponding to F51I,L+E56R+D57N+K98I+R118F+G163S+T231R+N233R and one or more (e.g., several) substitutions at positions corresponding to G23S, D27N, A40I, V60EK, N101D, Y220F, T244E and P256T.

In a further more preferred embodiment the variant comprises substitutions at positions corresponding to F51I,L+E56R+D57N+K98I+R118F+G163S+T231R+N233R+P256T and one or more (e.g., several) substitutions at positions corresponding to G23S, D27N, A40I, V60EK, N101D, Y220F, and T244E.

In a further even more preferred embodiment the variant comprises substitutions at positions corresponding to F51I,L+E56R+D57N+K98I+R118F+G163S+T231R+N233R+T244E and one or more (e.g., several) substitutions at positions corresponding to G23S, D27N, A40I,V60E,K, N101D, Y220F and +P256T.

In a further even more preferred embodiment the variant comprises substitutions at positions corresponding to F51I,L+E56R+D57N+K98I+R118F+G163S+T231R+N233R+T244E+P256T and one or more (e.g., several) substitutions at positions corresponding to G23S, D27N, A40I,V60E,K, N101D and Y220F.

In a further even more preferred embodiment the variant comprises substitutions at positions corresponding to F51I,L+E56R+D57N+K98I+R118F+G163S+T231R+N233R+T244E+P256T and one or more (e.g., several) substitutions at positions corresponding to G23S, D27N, A40I, V60E,K, N101D, and Y220F.

In a further preferred embodiments the variant comprises substitutions at positions corresponding to F51I,L+E56R+D57N+V60E,K+K98I+R118F+T231R+N233R and one or more (e.g., several) substitutions at positions corresponding to G23S, D27N, A40I, N101D, G163S, Y220F, T244E and P256T.

In a further preferred embodiments the variant comprises substitutions at positions corresponding to F51I,L+E56R+ D57N+V60E,K+K98I+R118F+T231R+N233R+P256T and one or more (e.g., several) substitutions at positions corresponding to G23S, D27N, A40I, N101D, G163S, Y220F, and T244E.

In a further preferred embodiments the variant comprises substitutions at positions corresponding to F51I,L+E56R+ D57N+V60E,K+K98I+N101D+R118F+T231R+N233R+ P256T and one or more (e.g., several) substitutions at positions corresponding to G23S, D27N, A40I, G163S, Y220F, and T244E.

In a further preferred embodiments the variant comprises substitutions at positions corresponding to F51I,L+E56R+ D57N+N101D+K98I+R118F+T231R+N233R+P256T and one or more (e.g., several) substitutions at positions corresponding to G23S, D27N, A40I, V60E,K, N101D, G163S, Y220F, and T244E.

Particularly preferred embodiments include variants comprising substitutions at positions corresponding to one of the following set of substitutions:
R118F+T231R+N233R+P256T;
A40I+R118F+T231R+N233R;
F51I+E56R+R118F+T231R+N233R;
F51L+E56R+R118F+T231R+N233R;
E56R+D57N+R118F+T231R+N233R;
E56R+V60K+R118F+T231R+N233R;
G23S+E56R+R118F+T231R+N233R;
D27N+E56R+R118F+T231R+N233R;
F51I+E56R+R118F+T231R+N233R;
E56R+R118F+T231R+N233R+P256T;
G23S+D27N+E56R+R118F+T231R+N233R;
G23S+F51I+E56R+R118F+T231R+N233R;
G23S+E56R+R118F+T231R+N233R+P256T;
D27N+F51I+E56R+R118F+T231R+N233R;
D27N+E56R+R118F+T231R+N233R+P256T;
F51I+E56R+R118F+T231R+N233R+P256T;
G23S+D27N+F51I+E56R+R118F+T231R+N233R;
G23S+D27N+E56R+R118F+T231R+N233R+P256T;
G23S+D27N+F51I+E56R+V60K+R118F+T231R+ N233R+P256T;
G23S+D27N+F51I+E56R+V60E+R118F+T231R+N233R+ P256T;
G23S+F51I+E56R+R118F+T231R+N233R+P256T;
D27N+F51I+E56R+R118F+T231R+N233R+P256T;
G23S+D27N+F51I+E56R+R118F+T231R+N233R+P256T;
A40I+E56R+R118F+T231R+N233R;
F51L+E56R+R118F+T231R+N233R;
D57N+E56R+R118F+T231R+N233R;
K98I+E56R+R118F+T231R+N233R;
G163S+E56R+R118F+T231R+N233R;
A40I+F51L+E56R+R118F+T231R+N233R;
A40I+D57N+E56R+R118F+T231R+N233R;
A40I+K98I+E56R+R118F+T231R+N233R;
A40I+G163S+E56R+R118F+T231R+N233R;
A40I+E56R+R118F+T231R+N233R+P256T;
F51L+D57N+E56R+R118F+T231R+N233R;
F51L+K98I+E56R+R118F+T231R+N233R;
F51L+G163S+E56R+R118F+T231R+N233R;
F51L+E56R+R118F+T231R+N233R+P256T;
D57N+K98I+E56R+R118F+T231R+N233R;
D57N+G163S+E56R+R118F+T231R+N233R;
D57N+E56R+R118F+T231R+N233R+P256T;
K98I+G163S+E56R+R118F+T231R+N233R;
K98I+E56R+R118F+T231R+N233R+P256T;
G163S+E56R+R118F+T231R+N233R+P256T;
A40I+F51L+D57N+E56R+R118F+T231R+N233R;
A40I+F51L+K98I+E56R+R118F+T231R+N233R;
A40I+F51L+G163S+E56R+R118F+T231R+N233R;
A40I+F51L+E56R+R118F+T231R+N233R+P256T;
A40I+D57N+K98I+E56R+R118F+T231R+N233R;
A40I+D57N+G163S+E56R+R118F+T231R+N233R;
A40I+D57N+E56R+R118F+T231R+N233R+P256T;
A40I+K98I+G163S+E56R+R118F+T231R+N233R;
A40I+K98I+E56R+R118F+T231R+N233R+P256T;
A40I+G163S+E56R+R118F+T231R+N233R+P256T;
F51L+D57N+K98I+E56R+R118F+T231R+N233R;
F51L+D57N+G163S+E56R+R118F+T231R+N233R;
F51L+D57N+E56R+R118F+T231R+N233R+P256T;
F51L+K98I+G163S+E56R+R118F+T231R+N233R;
F51L+K98I+E56R+R118F+T231R+N233R+P256T;
F51L+G163S+E56R+R118F+T231R+N233R+P256T;
D57N+K98I+G163S+E56R+R118F+T231R+N233R;
D57N+K98I+E56R+R118F+T231R+N233R+P256T;
D57N+G163S+E56R+R118F+T231R+N233R+P256T;
K98I+G163S+E56R+R118F+T231R+N233R+P256T;
A40I+F51L+D57N+K98I+E56R+R118F+T231R+N233R;
A40I+F51L+D57N+G163S+E56R+R118F+T231R+ N233R;
A40I+F51L+D57N+E56R+R118F+T231R+N233R+ P256T;
A40I+F51L+K98I+G163S+E56R+R118F+T231R+N233R;
A40I+F51L+K98I+E56R+R118F+T231R+N233R+P256T;
A40I+F51L+G163S+E56R+R118F+T231R+N233R+ P256T;
A40I+D57N+K98I+G163S+E56R+R118F+T231R+ N233R;
A40I+D57N+K98I+E56R+R118F+T231R+N233R+P256T;
A40I+D57N+G163S+E56R+R118F+T231R+N233R+ P256T;
A40I+K98I+G163S+E56R+R118F+T231R+N233R+ P256T;
F51L+D57N+K98I+G163S+E56R+R118F+T231R+ N233R;
F51L+D57N+K98I+E56R+R118F+T231R+N233R+ P256T;
F51L+D57N+G163S+E56R+R118F+T231R+N233R+ P256T;
F51L+K98I+G163S+E56R+R118F+T231R+N233R+ P256T;
D57N+K98I+G163S+E56R+R118F+T231R+N233R+ P256T;
A40I+F51L+D57N+K98I+G163S+E56R+R118F+T231R+ N233R;
A40I+F51L+D57N+K98I+E56R+R118F+T231R+N233R+ P256T;
A40I+F51L+D57N+G163S+E56R+R118F+T231R+ N233R+P256T;
A40I+F51L+K98I+G163S+E56R+R118F+T231R+ N233R+P256T;
A40I+D57N+K98I+G163S+E56R+R118F+T231R+ N233R+P256T;
F51L+D57N+K98I+G163S+E56R+R118F+T231R+ N233R+P256T;
A40I+F51L+D57N+K98I+G163S+E56R+R118F+T231R+ N233R+P256T;
A40I+F51L+E56R+D57N+K98I+R118F+G163S+T231R+ N233R+P256T;
A40I+E56R+R118F+T231R+N233R;
E56R+R118F+T231R+N233R+T244E;
G23S+D27N+E56R+R118F+T231R+N233R;

G23S+A40I+E56R+R118F+T231R+N233R;
G23S+F51I+E56R+R118F+T231R+N233R;
G23S+E56R+R118F+T231R+N233R+T244E;
G23S+E56R+R118F+T231R+N233R+P256T;
D27N+A40I+E56R+R118F+T231R+N233R;
D27N+F51I+E56R+R118F+T231R+N233R;
D27N+E56R+R118F+T231R+N233R+T244E;
D27N+E56R+R118F+T231R+N233R+P256T;
A40I+F51I+E56R+R118F+T231R+N233R;
A40I+E56R+R118F+T231R+N233R+T244E;
A40I+E56R+R118F+T231R+N233R+P256T;
F51I+E56R+R118F+T231R+N233R+T244E;
F51I+E56R+R118F+T231R+N233R+P256T;
E56R+R118F+T231R+N233R+T244E+P256T;
G23S+D27N+A40I+E56R+R118F+T231R+N233R;
G23S+D27N+A40I+E56R+V60K+R118F+T231R+N233R;
G23S+D27N+A40I+E56R+V60E+R118F+T231R+N233R;
G23S+D27N+F51I+E56R+R118F+T231R+N233R;
G23S+D27N+E56R+R118F+T231R+N233R+T244E;
G23S+D27N+E56R+R118F+T231R+N233R+P256T;
G23S+A40I+F51I+E56R+R118F+T231R+N233R;
G23S+A40I+E56R+R118F+T231R+N233R+T244E;
G23S+A40I+E56R+R118F+T231R+N233R+P256T;
G23S+F51I+E56R+R118F+T231R+N233R+T244E;
G23S+F51I+E56R+R118F+T231R+N233R+P256T;
G23S+E56R+R118F+T231R+N233R+T244E+P256T;
G23S+E56R+V60K+R118F+T231R+N233R+T244E+P256T;
G23S+E56R+V60E+R118F+T231R+N233R+T244E+P256T;
D27N+A40I+F51I+E56R+R118F+T231R+N233R;
D27N+A40I+E56R+R118F+T231R+N233R+T244E;
D27N+A40I+E56R+R118F+T231R+N233R+P256T;
D27N+F51I+E56R+R118F+T231R+N233R+T244E;
D27N+F51I+E56R+R118F+T231R+N233R+P256T;
D27N+E56R+R118F+T231R+N233R+T244E+P256T;
A40I+F51I+E56R+R118F+T231R+N233R+T244E;
A40I+F51I+E56R+R118F+T231R+N233R+P256T;
A40I+E56R+R118F+T231R+N233R+T244E+P256T;
F51I+E56R+R118F+T231R+N233R+T244E+P256T;
F51I+E56R+V60K+R118F+T231R+N233R+T244E+P256T;
F51I+E56R+V60E+R118F+T231R+N233R+T244E+P256T;
G23S+D27N+A40I+F51I+E56R+R118F+T231R+N233R;
G23S+D27N+A40I+F51I+E56R+V60K+R118F+T231R+N233R;
G23S+D27N+A40I+F51I+E56R+V60E+R118F+T231R+N233R;
G23S+D27N+A40I+E56R+R118F+T231R+N233R+T244E;
G23S+D27N+A40I+E56R+V60K+R118F+T231R+N233R+T244E;
G23S+D27N+A40I+E56R+V60E+R118F+T231R+N233R+T244E;
G23S+D27N+A40I+E56R+R118F+T231R+N233R+P256T;
G23S+D27N+F51I+E56R+R118F+T231R+N233R+T244E;
G23S+D27N+F51I+E56R+R118F+T231R+N233R+P256T;
G23S+D27N+E56R+R118F+T231R+N233R+T244E+P256T;
G23S+A40I+F51I+E56R+R118F+T231R+N233R+T244E;
G23S+A40I+F51I+E56R+R118F+T231R+N233R+P256T;
G23S+A40I+E56R+R118F+T231R+N233R+T244E+P256T;
G23S+F51I+E56R+R118F+T231R+N233R+T244E+P256T;
D27N+A40I+F51I+E56R+R118F+T231R+N233R+T244E;
D27N+A40I+F51I+E56R+R118F+T231R+N233R+P256T;
D27N+A40I+E56R+R118F+T231R+N233R+T244E+P256T;
D27N+F51I+E56R+R118F+T231R+N233R+T244E+P256T;
A40I+F51I+E56R+R118F+T231R+N233R+T244E+P256T;
A40I+F51I+E56R+V60K+R118F+T231R+N233R+T244E+P256T;
A40I+F51I+E56R+V60E+R118F+T231R+N233R+T244E+P256T;
G23S+D27N+A40I+F51I+E56R+R118F+T231R+N233R+T244E;
G23S+D27N+A40I+F51I+E56R+V60K+R118F+T231R+N233R+T244E;
G23S+D27N+A40I+F51I+E56R+R118F+T231R+N233R+P256T;
G23S+D27N+A40I+F51I+E56R+V60K+R118F+T231R+N233R+P256T;
G23S+D27N+A40I+F51I+E56R+V60E+R118F+T231R+N233R+P256T;
G23S+D27N+A40I+F51I+E56R+R118F+T231R+N233R+T244E+P256T;
G23S+D27N+F51I+E56R+R118F+T231R+N233R+T244E+P256T;
G23S+A40I+F51I+E56R+R118F+T231R+N233R+T244E+P256T;
D27N+A40I+F51I+E56R+R118F+T231R+N233R+T244E+P256T;
D27N+A40I+F51I+E56R+V60K+R118F+T231R+N233R+T244E+P256T;
D27N+A40I+F51I+E56R+V60E+R118F+T231R+N233R+T244E+P256T;
G23S+D27N+A40I+F51I+E56R+R118F+T231R+N233R+T244E+P256T;
G23S+D27N+A40I+F51I+E56R+K98I+N101D+R118F+T231R+N233R+T244E+P256T;
G23S+D27N+A40I+F51I+E56R+V60K+R118F+T231R+N233R+T244E+P256T;
G23S+D27N+A40I+F51I+E56R+V60E+R118F+T231R+N233R+T244E+P256T;
F51I+E56R+R118F+T231R+N233R;
E56R+R118F+T231R+N233R+T244E;
D27N+F51I+E56R+R118F+T231R+N233R;
D27N+E56R+R118F+T231R+N233R+T244E;
F51I+E56R+R118F+T231R+N233R+T244E;
D27N+F51I+E56R+R118F+T231R+N233R+T244E;
G23S+E56R+R118F+T231R+N233R;
D27N+E56R+R118F+T231R+N233R;
K98I+E56R+R118F+T231R+N233R;
Y220F+E56R+R118F+T231R+N233R;
E56R+R118F+T231R+N233R+T244E;
G23S+D27N+E56R+R118F+T231R+N233R;
G23S+F51I+E56R+R118F+T231R+N233R;
G23S+K98I+E56R+R118F+T231R+N233R;
G23S+Y220F+E56R+R118F+T231R+N233R;
G23S+E56R+R118F+T231R+N233R+T244E;
G23S+E56R+R118F+T231R+N233R+P256T;
D27N+F51I+E56R+R118F+T231R+N233R;
D27N+K98I+E56R+R118F+T231R+N233R;
D27N+Y220F+E56R+R118F+T231R+N233R;
D27N+E56R+R118F+T231R+N233R+T244E;
D27N+E56R+R118F+T231R+N233R+P256T;
F51I+K98I+E56R+R118F+T231R+N233R;

F51I+Y220F+E56R+R118F+T231R+N233R;
F51I+E56R+R118F+T231R+N233R+T244E;
F51I+E56R+R118F+T231R+N233R+P256T;
K98I+Y220F+E56R+R118F+T231R+N233R;
K98I+E56R+R118F+T231R+N233R+T244E;
K98I+E56R+R118F+T231R+N233R+P256T;
Y220F+E56R+R118F+T231R+N233R+T244E;
Y220F+E56R+R118F+T231R+N233R+P256T;
E56R+R118F+T231R+N233R+T244E+P256T;
G23S+D27N+F51I+E56R+R118F+T231R+N233R;
G23S+D27N+K98I+E56R+R118F+T231R+N233R;
G23S+D27N+Y220F+E56R+R118F+T231R+N233R;
G23S+D27N+E56R+R118F+T231R+N233R+T244E;
G23S+D27N+E56R+R118F+T231R+N233R+P256T;
G23S+F51I+K98I+E56R+R118F+T231R+N233R;
G23S+F51I+Y220F+E56R+R118F+T231R+N233R;
G23S+F51I+E56R+R118F+T231R+N233R+T244E;
G23S+F51I+E56R+R118F+T231R+N233R+P256T;
G23S+K98I+Y220F+E56R+R118F+T231R+N233R;
G23S+K98I+E56R+R118F+T231R+N233R+T244E;
G23S+K98I+E56R+R118F+T231R+N233R+P256T;
G23S+Y220F+E56R+R118F+T231R+N233R+T244E;
G23S+Y220F+E56R+R118F+T231R+N233R+P256T;
G23S+E56R+R118F+T231R+N233R+T244E+P256T;
D27N+F51I+K98I+E56R+R118F+T231R+N233R;
D27N+F51I+Y220F+E56R+R118F+T231R+N233R;
D27N+F51I+E56R+R118F+T231R+N233R+T244E;
D27N+F51I+E56R+R118F+T231R+N233R+P256T;
D27N+K98I+Y220F+E56R+R118F+T231R+N233R;
D27N+K98I+E56R+R118F+T231R+N233R+T244E;
D27N+K98I+E56R+R118F+T231R+N233R+P256T;
D27N+Y220F+E56R+R118F+T231R+N233R+T244E;
D27N+Y220F+E56R+R118F+T231R+N233R+P256T;
D27N+E56R+R118F+T231R+N233R+T244E+P256T;
F51I+K98I+Y220F+E56R+R118F+T231R+N233R;
F51I+K98I+E56R+R118F+T231R+N233R+T244E;
F51I+K98I+E56R+R118F+T231R+N233R+P256T;
F51I+Y220F+E56R+R118F+T231R+N233R+T244E;
F51I+Y220F+E56R+R118F+T231R+N233R+P256T;
F51I+E56R+R118F+T231R+N233R+T244E+P256T;
K98I+Y220F+E56R+R118F+T231R+N233R+T244E;
K98I+Y220F+E56R+R118F+T231R+N233R+P256T;
K98I+E56R+R118F+T231R+N233R+T244E+P256T;
Y220F+E56R+R118F+T231R+N233R+T244E+P256T;
G23S+D27N+F51I+K98I+E56R+R118F+T231R+N233R;
G23S+D27N+F51I+Y220F+E56R+R118F+T231R+N233R;
G23S+D27N+F51I+E56R+R118F+T231R+N233R+T244E;
G23S+D27N+F51I+E56R+R118F+T231R+N233R+P256T;
G23S+D27N+K98I+Y220F+E56R+R118F+T231R+N233R;
G23S+D27N+K98I+E56R+R118F+T231R+N233R+T244E;
G23S+D27N+K98I+E56R+R118F+T231R+N233R+P256T;
G23S+D27N+Y220F+E56R+R118F+T231R+N233R+T244E;
G23S+D27N+Y220F+E56R+R118F+T231R+N233R+P256T;
G23S+D27N+E56R+R118F+T231R+N233R+T244E+P256T;
G23S+F51I+K98I+Y220F+E56R+R118F+T231R+N233R;
G23S+F51I+K98I+E56R+R118F+T231R+N233R+T244E;
G23S+F51I+K98I+E56R+R118F+T231R+N233R+P256T;
G23S+F51I+Y220F+E56R+R118F+T231R+N233R+T244E;
G23S+F51I+Y220F+E56R+R118F+T231R+N233R+P256T;
G23S+F51I+E56R+R118F+T231R+N233R+T244E+P256T;
G23S+K98I+Y220F+E56R+R118F+T231R+N233R+T244E;
G23S+K98I+Y220F+E56R+R118F+T231R+N233R+P256T;
G23S+K98I+E56R+R118F+T231R+N233R+T244E+P256T;
G23S+Y220F+E56R+R118F+T231R+N233R+T244E+P256T;
D27N+F51I+K98I+Y220F+E56R+R118F+T231R+N233R;
D27N+F51I+K98I+E56R+R118F+T231R+N233R+T244E;
D27N+F51I+K98I+E56R+R118F+T231R+N233R+P256T;
D27N+F51I+Y220F+E56R+R118F+T231R+N233R+T244E;
D27N+F51I+Y220F+E56R+R118F+T231R+N233R+P256T;
D27N+F51I+E56R+R118F+T231R+N233R+T244E+P256T;
D27N+K98I+Y220F+E56R+R118F+T231R+N233R+T244E;
D27N+K98I+Y220F+E56R+R118F+T231R+N233R+P256T;
D27N+K98I+E56R+R118F+T231R+N233R+T244E+P256T;
D27N+Y220F+E56R+R118F+T231R+N233R+T244E+P256T;
F51I+K98I+Y220F+E56R+R118F+T231R+N233R+T244E;
F51I+K98I+Y220F+E56R+R118F+T231R+N233R+P256T;
F51I+K98I+E56R+R118F+T231R+N233R+T244E+P256T;
F51I+Y220F+E56R+R118F+T231R+N233R+T244E+P256T;
K98I+Y220F+E56R+R118F+T231R+N233R+T244E+P256T;
G23S+D27N+F51I+K98I+Y220F+E56R+R118F+T231R+N233R;
G23S+D27N+F51I+K98I+E56R+R118F+T231R+N233R+T244E;
G23S+D27N+F51I+K98I+E56R+R118F+T231R+N233R+P256T;
G23S+D27N+F51I+Y220F+E56R+R118F+T231R+N233R+T244E;
G23S+D27N+F51I+Y220F+E56R+R118F+T231R+N233R+P256T;
G23S+D27N+F51I+E56R+R118F+T231R+N233R+T244E+P256T;
G23S+D27N+K98I+Y220F+E56R+R118F+T231R+N233R+T244E;
G23S+D27N+K98I+Y220F+E56R+R118F+T231R+N233R+P256T;
G23S+D27N+K98I+E56R+R118F+T231R+N233R+T244E+P256T;
G23S+D27N+Y220F+E56R+R118F+T231R+N233R+T244E+P256T;
G23S+F51I+K98I+Y220F+E56R+R118F+T231R+N233R+T244E;
G23S+F51I+K98I+Y220F+E56R+R118F+T231R+N233R+P256T;
G23S+F51I+K98I+E56R+R118F+T231R+N233R+T244E+P256T;
G23S+F51I+Y220F+E56R+R118F+T231R+N233R+T244E+P256T;

G23S+K98I+Y220F+E56R+R118F+T231R+N233R+
T244E+P256T;
D27N+F51I+K98I+Y220F+E56R+R118F+T231R+
N233R+T244E;
D27N+F51I+K98I+Y220F+E56R+R118F+T231R+
N233R+P256T;
D27N+F51I+K98I+E56R+R118F+T231R+N233R+
T244E+P256T;
D27N+F51I+Y220F+E56R+R118F+T231R+N233R+
T244E+P256T;
D27N+K98I+Y220F+E56R+R118F+T231R+N233R+
T244E+P256T;
F51I+K98I+Y220F+E56R+R118F+T231R+N233R+
T244E+P256T;
G23S+D27N+F51I+K98I+Y220F+E56R+R118F+T231R+
N233R+T244E;
G23S+D27N+F51I+K98I+Y220F+E56R+R118F+T231R+
N233R+P256T;
G23S+D27N+F51I+K98I+E56R+R118F+T231R+N233R+
T244E+P256T;
G23S+D27N+F51I+Y220F+E56R+R118F+T231R+
N233R+T244E+P256T;
G23S+D27N+K98I+Y220F+E56R+R118F+T231R+
N233R+T244E+P256T;
G23S+F51I+K98I+Y220F+E56R+R118F+T231R+
N233R+T244E+P256T;
D27N+F51I+K98I+Y220F+E56R+R118F+T231R+
N233R+T244E+P256T;
G23S+D27N+F51I+K98I+Y220F+E56R+R118F+T231R+
N233R+T244E+P256T;
G23S+D27N+F51I+E56R+K98I+R118F+Y220F+
T231R+N233R+T244E+P256T.

The lipase variant preferably has at least 60%, at least 65%, at least 70%, at least 75%, at least 80%, at least 85%, at least 90%, at least 95% identity, at least 96%, at least 97%, at least 98%, or at least 99%, but less than 100% sequence identity to the parent lipase.

The variant preferably has at least 60%, at least 65%, at least 70%, at least 75%, at least 80%, at least 85%, at least 90%, at least 95% identity, at least 96%, at least 97%, at least 98%, or at least 99%, but less than 100% sequence identity to SEQ ID NO: 2.

The variant may have from 1-40, 1-30, 1-20, such as 1-12, such as 1-11, such as 1-10, such as 1-9, such as 1-8, such as 1-7, such as 1-6, such as 1-5, such as 1-4, such as 1-3, or such as 1, 2, 3, 4, 5, 6, 7, 8, 9, 10, 11, 12, 13, 14, 15, 16, 17, 18, 19, or 20 substitutions.

The variant may, in comparison to the parent lipase, have one or more of the following properties: improved wash performance, reduced odor generation, improved storage stability, longer shelf life and/or increased thermostability.

The lipase variant may further comprise one or more additional substitutions at one or more (e.g., several) other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for lipase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64.

The identity of essential amino acids can also be inferred from an alignment with a related polypeptide. The variants may consist or contain at least 50%, at least 55%, at least 60%, at least 65%, at least 70%, at least 75%, at least 80%, at least 85%, at least 90%, or at least 95% of the number of amino acids of SEQ ID NO: 2.

Parent Lipases

The parent lipase may be selected from the group consisting of:

a) a polypeptide having at least 60%, at least 65%, at least 70%, at least 75%, at least 80%, at least 85%, at least 90%, at least 95% identity, at least 96%, at least 97%, at least 98%, or at least 99% or 100% sequence identity to SEQ ID NO: 2;

b) a polypeptide encoded by a polynucleotide that hybridizes under low stringency conditions, medium stringency conditions, medium-high stringency conditions, high stringency conditions, or very high stringency conditions with (i) the polypeptide coding sequence of SEQ ID NO: 1 or (ii) the full-length complement of (i);

c) a polypeptide encoded by a polynucleotide having at least 60%, at least 65%, at least 70%, at least 75%, at least 80%, at least 85%, at least 90%, at least 95%, at least 96%, at least 97%, at least 98%, at least 99%, or 100% sequence identity to SEQ ID NO: 1; and d) a fragment of the polypeptide of SEQ ID NO: 2.

In an aspect of the invention, the parent lipase has a sequence identity to the polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have lipase activity.

In one aspect, the amino acid sequence of the parent differs by up to 40 amino acids, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 from the polypeptide of SEQ ID NO: 2.

In another aspect, the parent comprises or consists of the amino acid sequence of SEQ ID NO: 2.

In another aspect, the parent is a fragment of the polypeptide of SEQ ID NO: 2 containing at least 50%, at least 55%, at least 60%, at least 65%, at least 70%, at least 75%, at least 80%, at least 85%, at least 90%, or at least 95% of the number of amino acids of SEQ ID NO: 2.

In another embodiment, the parent is an allelic variant of the polypeptide of SEQ ID NO: 2.

In another aspect, the parent lipase is encoded by a polynucleotide that hybridizes under very low stringency conditions, low stringency conditions, medium stringency conditions, medium-high stringency conditions, high stringency conditions, or very high stringency conditions with (i) the polypeptide coding sequence of SEQ ID NO: 1, (ii) the full-length complement of (i) (Sambrook et al., 1989, *Molecular Cloning, A Laboratory Manual*, 2d edition, Cold Spring Harbor, N.Y.).

The polynucleotide of SEQ ID NO: 1 or a subsequence thereof, as well as the polypeptide of SEQ ID NO: 2 or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the polypeptide coding sequence of SEQ ID NO: 1; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the polypeptide coding sequence of SEQ ID NO: 1. In another aspect, the nucleic acid probe is at least 50%, at least 55%, at least 60%, at least 65%, at least 70%, at least 75%, at least 80%, at least 85%, at least 90%, or at least 95% of the number of nucleotides of SEQ ID NO: 1. In another aspect, the nucleic acid probe is a polynucleotide that encodes the polypeptide of SEQ ID NO: 2; the polypeptide thereof; or a fragment thereof. In another aspect, the nucleic acid probe is SEQ ID NO: 1.

In another embodiment, the parent is encoded by a polynucleotide having a sequence identity to the polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent lipase may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent lipase may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial lipase. For example, the parent may be a Gram-positive bacterial polypeptide such as a *Bacillus, Clostridium, Enterococcus, Geobacillus, Lactobacillus, Lactococcus, Oceanobacillus, Staphylococcus, Streptococcus, Streptomyces* or *Thermobifida* lipase, or a Gram-negative bacterial polypeptide such as a *Campylobacter, E. coli, Flavobacterium, Fusobacterium, Helicobacter, Ilyobacter, Neisseria, Pseudomonas, Salmonella,* or *Ureaplasma* lipase.

In one aspect, the parent is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* lipase.

In another aspect, the parent is a *Streptococcus equisimilis, Streptococcus pyogenes, Streptococcus uberis*, or *Streptococcus equi* subsp. *Zooepidemicus* lipase.

In another aspect, the parent is a *Streptomyces achromogenes, Streptomyces avermitilis, Streptomyces coelicolor, Streptomyces griseus*, or *Streptomyces lividans* lipase.

In another aspect, the parent is a *Thermobifida alba* or *Thermobifida fusca* (formerly known as *Thermomonaspora fusca*) lipase.

The parent may be a fungal lipase. For example, the parent may be a yeast lipase such as a *Candida, Kluyveromyces, Pichia, Saccharomyces, Schizosaccharomyces*, or *Yarrowia* lipase; or a filamentous fungal lipase such as an *Acremonium, Agaricus, Alternaria, Aspergillus, Aureobasidium, Botryosphaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptosparia, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella*, or *Xylaria* lipase.

In another aspect, the parent is a *Saccharomyces carlsbergensis, Saccharomyces cerevisiae, Saccharomyces diastaticus, Saccharomyces douglasii, Saccharomyces kluyveri, Saccharomyces norbensis*, or *Saccharomyces oviformis* lipase.

In another aspect, the parent is an *Acremonium cellulolyticus, Aspergillus aculeatus, Aspergillus awamori, Aspergillus foetidus, Aspergillus fumigatus, Aspergillus japonicus, Aspergillus nidulans, Aspergillus niger, Aspergillus oryzae, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia setosa, Thielavia spededonium, Thielavia subthermophila, Thielavia terrestris, Trichoderma harzianum, Trichoderma koningii, Trichoderma longibrachiatum, Trichoderma reesei*, or *Trichoderma viride* lipase.

In another aspect, the parent is a *Thermomyces lanuginosus* lipase, e.g., in particular the lipase of SEQ ID NO: 2.

It will be understood that for the aforementioned species, the variants useful in the invention encompass both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent lipase may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The variant useful in the present invention may be prepared by methods for obtaining lipase variants comprising: (a) introducing substitutions at positions corresponding to G23S, D27N, A40I, F51I,L, E56R, D57N, K98I, R118F, G163S, T231R, N233R, Y220F, T244E, and P256T; (b) selecting the variant which has lipase activity and in comparison with the parent lipase has one of the desired properties listed above; and (c) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more (e.g., several) mutations are introduced at one or more defined sites in a polynucleotide encoding the parent lipase.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent lipase and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., US2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO95/17413; or WO95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

The lipase variant may be made by a method comprising: (a) cultivating a host cell under conditions suitable for expression of the variant; and (b) recovering the variant.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

The polynucleotide may be manipulated in a variety of ways to provide for expression of a variant. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide which is recognized by a host cell for expression of the polynucleotide. The promoter contains transcriptional control sequences that mediate the expression of the variant. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO96/00787), *Fusarium venenatum* amyloglucosidase (WO00/56900), *Fusarium venenatum* Dania (WO00/56900), *Fusarium venenatum* Quinn (WO00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator sequence is operably linked to the 3'-terminus of the polynucleotide encoding the variant. Any terminator that is functional in the host cell may be used.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Sac-

*charomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader sequence is operably linked to the 5'-terminus of the polynucleotide encoding the variant. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the variant-encoding sequence and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a variant and directs the variant into the cell's secretory pathway. The 5'-end of the coding sequence of the polynucleotide may inherently contain a signal peptide coding sequence naturally linked in translation reading frame with the segment of the coding sequence that encodes the variant. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the variant. However, any signal peptide coding sequence that directs the expressed variant into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, Microbiological Reviews 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a variant. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of the variant and the signal peptide sequence is positioned next to the N-terminus of the propeptide sequence.

It may also be desirable to add regulatory sequences that regulate expression of the variant relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the variant would be operably linked with the regulatory sequence.

Expression Vectors

The application also discloses recombinant expression vectors comprising a polynucleotide encoding a variant useful in the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the variant at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, it is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the variant or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a variant. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present application also discloses recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the variant and its source.

The host cell may be any cell useful in the recombinant production of a variant, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus,*

*Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell, including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397), or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804) or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, Soc. App. Bacteriol. Symposium Series No. 9, 1980).

The yeast host cell may be a *Candida, Hansenula, Kluyveromyces, Pichia, Saccharomyces, Schizosaccharomyces*, or *Yarrowia* cell such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present application also discloses methods of producing a lipase variant of the present invention, comprising:

(a) cultivating a host cell of the present invention under conditions suitable for expression of the variant; and (b) recovering the variant.

The host cells are cultivated in a nutrient medium suitable for production of the variant using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the variant to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the variant is secreted into the nutrient medium, the variant can be recovered directly from the medium. If the variant is not secreted, it can be recovered from cell lysates.

The variant may be detected using methods known in the art that are specific for the variants. These detection methods include, but are not limited to, use of specific antibodies, formation of an enzyme product, or disappearance of an enzyme substrate. For example, an enzyme assay may be used to determine the activity of the variant such as those described in the examples.

The variant may be recovered using methods known in the art. For example, the variant may be recovered from the nutrient medium by conventional procedures including, but not limited to, collection, centrifugation, filtration, extraction, spray-drying, evaporation, or precipitation.

The variant may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure variants.

In an alternative aspect, the variant is not recovered, but rather a host cell of the present invention expressing the variant is used as a source of the variant.

Microcapsule Composition

In the present invention lipase, preferably the lipase variant, is optionally encapsulated in a microcapsule. The membrane of the microcapsule is preferably produced by cross-linking of a polybranched polyamine having a molecular weight of more than 1 kDa. The membrane formed by crosslinking the polybranched polyamine is capable of separating the enzyme from surfactants, particularly anionic surfactants in the detergent, which are known to be detrimental to the stability of enzymes.

Preferably when using encapsulated enzymes in detergents, the encapsulates are capable of releasing the enzyme substantially immediately upon dilution of the detergent in water, as for example in a laundry or dishwashing application. The preferred microcapsules have excellent properties in this regard, and preferably are capable of releasing the entire encapsulated enzyme within a minute.

Preferred microcapsules do not require the presence of a core polymer to be capable of releasing the enzyme, upon dilution in water. Further, the invention does not require the enzyme(s) to be in a precipitated form in the core of the microcapsule, in order to control premature release, as described in WO 97/24177.

When encapsulating a lipase variant as defined herein, and optionally other enzymes, in a microcapsule with a semipermeable membrane, and having a water activity inside these capsules (prior to addition to the liquid detergent) higher than in the liquid detergent, the capsules will undergo a (partly) collapse when added to detergent (water is oozing out), thus leaving a more concentrated and more viscous enzyme containing interior in the capsules. The collapse of the membrane may also result in a reduced permeability. This can be further utilized by addition of stabilizers/polymers, especially ones that are not permeable through the membrane. The collapse and resulting increase in viscosity will reduce/hinder the diffusion of hostile components (e.g., surfactants or sequestrants) into the capsules, and thus increase the storage stability of the enzyme in liquid detergent. Components in liquid detergent that are sensitive to the enzyme (e.g., components that act as substrate for the enzyme) are also protected against degradation by the enzyme. During wash the liquid detergent is diluted by water, thus increasing the water activity. Water will now diffuse into the capsules (osmosis). The capsules will swell and the membrane will either become permeable to the enzyme so they can leave the capsules, or simply burst and in this way releasing the enzyme. The concept is very efficient in stabilizing the enzymes against hostile components in liquid detergent, and vice versa also protects enzyme sensitive components in the liquid detergent from enzymes.

Examples of detergent components which are sensitive to, and can be degraded by, enzymes include (relevant enzyme in parenthesis): xanthan gum (xanthanase), polymers with ester bonds (lipase), hydrogenated castor oil (lipase), perfume (lipase), methyl ester sulfonate surfactants (lipase), cellulose and cellulose derivatives (e.g. CMC) (cellulase), and dextrin and cyclodextrin (amylase).

Also, sensitive detergent ingredients can be encapsulated, and thus stabilized, in the microcapsules described herein. Sensitive detergent ingredients are prone to degradation during storage. Such detergent ingredients include bleaching compounds, bleach activators, perfumes, polymers, builder, surfactants, etc.

Generally, the microcapsules described herein can be used to separate incompatible/sensitive components/compounds in the detergent composition.

Addition of the microcapsules to the detergent composition may be used to influence the visual appearance of the detergent composition or unit dose article, for example by providing an opacifying effect (using small microcapsules) or an effect of distinctly visible particles (using large microcapsules). The microcapsules may optionally be colored.

The microcapsules may be used to reduce the enzyme dust levels during handling and processing of enzyme products.

Unless otherwise indicated, all percentages are indicated as percent by weight (% w/w) throughout the application.

Preparation of the Microcapsule

The preferred microcapsules are typically produced by forming water droplets into a continuum that is non-miscible with water—i.e., typically by preparing a water-in-oil emulsion—and subsequently formation of the membrane by interfacial polymerization via addition of a cross-linking agent. After eventual curing the capsules can be harvested and further rinsed and formulated by methods known in the art. The capsule formulation is subsequently added to the detergent.

The payload, the major membrane constituents and eventual additional component that are to be encapsulated are found in the water phase. In the continuum is found components that stabilize the water droplets towards coalescence (emulsifiers, emulsion stabilizers, surfactants etc.) and the cross-linking agent is also added via the continuum.

The emulsion can be prepared be any methods known in the art, e.g., by mechanical agitation, dripping processes, membrane emulsification, microfluidics, sonication etc. In some cases simple mixing of the phases automatically will result in an emulsion, often referred to as self-emulsification. Using methods resulting in a narrow size distribution is an advantage.

The cross-linking agent(s) is typically subsequently added to the emulsion, either directly or more typically by preparing a solution of the crosslinking agent in a solvent which is soluble in the continuous phase. The emulsion and cross-linking agent or solution hereof can be mixed by conventional methods used in the art, e.g., by simple mixing or by carefully controlling the flows of the emulsion and the cross-linking agent solution through an in-line mixer.

In some cases curing of the capsules may be needed to complete the membrane formation. Curing may be effected by simple stirring of the capsules for some time to allow the interfacial polymerization reaction to end. In other cases the membrane formation can be stopped by addition of reaction quencher.

The capsules may be post-modified, e.g., by reacting components onto the membrane to hinder or reduce flocculation of the particles in the detergent as described in WO 99/01534.

The produced capsules can be isolated or concentrated by methods known in the art, e.g., by filtration, centrifugation, distillation or decantation of the capsule dispersion.

The resulting capsules can be further formulated, e.g., by addition of surfactants to give the product the desired properties for storage, transport and later handling and addition to the detergent. Other microcapsule formulation agents include rheology modifiers, biocides (e.g., Proxel), acid/base for adjustment of pH (which will also adjust inside the microcapsules), and water for adjustment of water activity.

The capsule forming process may include the following steps:
Preparation of the initial water and oil phase(s),
Forming a water-in-oil emulsion,
Membrane formation by interfacial polymerization,
Optional post modification,
Optional isolation and/or formulation,
Addition to detergent.

The process can be either a batch process or a continuous or semi-continuous process.

As described herein a microcapsule is a small aqueous sphere having a substantially uniform membrane around it. The material inside the microcapsule is referred to as the core, internal phase, or fill, whereas the membrane is sometimes called a shell, coating, or wall. The preferred microcapsules described herein have diameters between 0.5 µm and 2 millimeters. Preferably, the mean diameter of the microcapsules is in the range of 1 µm to 1000 µm, more preferably in the range of 5 µm to 500 µm, even more preferably in the range of 10 µm to 500 µm, even more preferably in the range of 50 µm to 500 µm, and most preferably in the range of 50 µm to 200 µm. Alternatively, the diameter of the microcapsules is in the range of 0.5 µm to 30 µm; or in the range of 1 µm to 25 µm. The diameter of the microcapsule is measured in the oil phase after polymerization is complete. The diameter of the capsule may change depending on the water activity of the surrounding chemical environment.

Microencapsulation of enzymes, as may be used in the present invention, may be carried out by interfacial polymerization, wherein the two reactants in a polymerization reaction meet at an interface and react rapidly. The basis of this method is a reaction of a polyamine with an acid derivative, usually an acid halide, acting as a crosslinking agent. The polyamine is preferably substantially water-soluble (when in free base form). Under the right conditions, thin flexible membranes form rapidly at the interface. One way of carrying out the polymerization is to use an aqueous solution of the enzyme and the polyamine, which are emulsified with a non-aqueous solvent (and an emulsifier), and a solution containing the acid derivative is added. An alkaline agent may be present in the enzyme solution to neutralize the acid formed during the reaction. Polymer (polyamide) membranes form instantly at the interface of the emulsion droplets. The polymer membrane of the microcapsule is typically of a cationic nature, and thus bind/complex with compounds of an anionic nature.

The diameter of the microcapsules is determined by the size of the emulsion droplets, which is controlled, for example by the stirring rate.

Emulsion

An emulsion is a temporary or permanent dispersion of one liquid phase within a second liquid phase. The second liquid is generally referred to as the continuous phase. Surfactants are commonly used to aid in the formation and stabilization of emulsions. Not all surfactants are equally able to stabilize an emulsion. The type and amount of a surfactant needs to be selected for optimum emulsion utility especially with regard to preparation and physical stability of the emulsion, and stability during dilution and further processing. Physical stability refers to maintaining an emulsion in a dispersion form. Processes such as coalescence, aggregation, adsorption to container walls, sedimentation and creaming, are forms of physical instability, and should be avoided. Examples of suitable surfactants are described in WO 97/24177, page 19-21; and in WO 99/01534.

Emulsions can be further classified as either simple emulsions, wherein the dispersed liquid phase is a simple homogeneous liquid, or a more complex emulsion, wherein the dispersed liquid phase is a heterogeneous combination of liquid or solid phases, such as a double emulsion or a multiple-emulsion. For example, a water-in-oil double emulsion or multiple emulsion may be formed wherein the water phase itself further contains an emulsified oil phase; this type of emulsion may be specified as an oil-in-water-in oil (o/w/o) emulsion. Alternatively, a water-in-oil emulsion may be formed wherein the water phase contains a dispersed solid phase often referred to as a suspension-emulsion. Other more complex emulsions can be described. Because of the inherent difficulty in describing such systems, the term emulsion is used to describe both simple and more complex emulsions without necessarily limiting the form of the emulsion or the type and number of phases present Polyamine The rigidity/flexibility and permeability of the membrane is mainly influenced by the choice of polyamine. The preferred polyamine used for encapsulation as described herein comprises a polybranched polyamine. Each branch, preferably ending with a primary amino group serves as a tethering point in the membrane network, thereby giving the favorable properties of the invention. A polybranched polyamine as described herein preferably comprises a polyamine having more than two branching points and more than two reactive amino groups (capable of reacting with the crosslinking agent, i.e., primary and secondary amino groups). For preparation of the preferred microcapsules, the polybranched polyamine is used as starting material when the emulsion is prepared—it is not formed in situ from other starting materials. To obtain the attractive properties of the preferred microcapsules, the polybranched structure of the polyamine must be present as starting material.

There is a close relation between number of branching points and number of primary amines, since primary amines will always be positioned at the end of a branch: a linear amine can only contain two primary amines. For each branching point hypothetically introduced in such a linear di-amine will allow one or more primary amine(s) to be introduced at the end of the introduced branch(es). In this context we understand the primary amino group as part of the branch, i.e., the endpoint of the branch. For example, we consider both tris(2-aminoethyl)amine and 1,2,3-propanetriamine as molecules having one branching point. For the preferred microcapsules, the polyamine has at least four primary amines. Branching points can be introduced from an aliphatic hydrocarbon chain as in the previously stated examples or from unsaturated carbon bonds, such as in, e.g., 3,3'-diaminobenzidine, or from tertiary amino groups, such as in N,N,N',N'-tetrakis-(2-aminoethyl)ethylenediamine.

Preferably, the polybranched polyamine is not a peptide or protein. Preferably the reactive amino groups constitute at least 15% of the molecular weight of the polybranched polyamine, such as more than 20%, or more than 25%. Preferably, the molecular weight of the polybranched polyamine is at least 1 kDa; more preferably, the molecular weight of the polybranched polyamine is at least 1.3 kDa. Preferably the polybranched polyamine is a polyethyleneimine (PEI), and modifications thereof, having more than two branching points and more than two reactive amino groups; wherein the reactive amino groups constitute at least 15% of the molecular weight of the PEI, such as more than 20%, or more than 25%. Preferably, the molecular weight of the PEI is at least 1 kDa. Combinations of different polybranched polyamines may be used for preparing the microcapsule.

The advantageous properties (e.g., enzyme storage stability, reduced enzyme leakage, reduced in-flux of detergent ingredients) of the microcapsule may be improved by adding one or more small amines with a molecular weight of less than 1 kDa. The small amine is preferably substantially water-soluble (when in free base form) and can be a material such as ethylene diamine, hexamethylene diamine, hexane diamine, diethylene tetramine, ethylene tetramine, diamino benzene, piperazine, tetramethylene pentamine or, preferably, diethylene triamine (DETA). The small amines may be added in an amount of up to 50%, preferably up to 40%, up to 30%, up to 20%, up to 10%, or up to 5%, by weight of the total content of small amine and polybranched polyamine, when preparing the microcapsule of the invention.

A preferred cross-linking agent comprises a molecule having at least two groups/sites capable of reacting with amines to form covalent bonds. The crosslinking agent is preferably oil soluble and can be in the form of an acid anhydride or acid halide, preferably an acid chloride. For example, it can be adipoyl chloride, sebacoyl chloride, dodecanedioc acid chloride, phthaloyl chloride, terephthaloyl chloride, isophthaloyl chloride, or trimesoyl chloride; but preferably, the crosslinking agent is terephthaloyl chloride or trimesoyl chloride.

In a specifically contemplated embodiment, the microcapsule composition of the invention is one described in WO 2014/177709 (hereby incorporated by reference) comprising a lipase variant of the invention. As also mentioned above the microcapsules may further include an alcohol, such as a polyol. In preferred microcapsules, (a) comprises a polyethyleneimine. In a preferred microcapsule, (b) comprises an ethyleneamine or alkanolamine. In an preferred embodiment (b) is selected from the group consisting of ethylene diamine, diethylene triamine, triethylene tetraamine, bis(3-aminopropyl)amine, monoethanolamine, diethanolamine, triethanolamine, hexamethylene diamine, diamino benzene, piperazine, and tetraethylene pentaamine, more preferably (b) is selected from the group consisting of diethylene triamine, triethylene tetraamine, bis(3-aminopropyl)amine, monoethanolamine, and diethanolamine. Preferably the microcapsule comprises a source of $Mg^{2+}$, $Ca^{2+}$, or $Zn^{2+}$ ions, such as a poorly soluble salt of $Mg^{2+}$, $Ca^{2+}$, or $Zn^{2+}$. Preferably an acid chloride is used as crosslinking agent, such as isophtaloyl chloride, terephthaloyl chloride, or trimesoyl chloride. In a preferred embodiment, the membrane is produced by interfacial polymerization.

Suitable microcapsules are described in WO 2015/1144784 (hereby incorporated by reference) comprising a lipase variant as described herein.

Detergent Compositions

Preferred detergent compositions are laundry detergent compositions for cleaning and/or treating fabric. The preferred detergent compositions are in liquid form. The invention is particularly directed to a water-soluble unit dose article comprising a water-soluble film and a detergent composition, preferably a liquid laundry detergent composition.

Water-Soluble Unit Dose Article

The water-soluble film and the liquid detergent composition are described in more detail below.

The water-soluble unit dose article comprises the water-soluble film shaped such that the unit-dose article comprises at least one internal compartment surrounded by the water-soluble film. The unit dose article may comprise a first water-soluble film and a second water-soluble film sealed to one another such to define the internal compartment. The water-soluble unit dose article is constructed such that the detergent composition does not leak out of the compartment during storage. However, upon addition of the water-soluble unit dose article to water, the water-soluble film dissolves and releases the contents of the internal compartment into the wash liquor.

The compartment should be understood as meaning a closed internal space within the unit dose article, which holds the detergent composition. During manufacture, a first water-soluble film may be shaped to comprise an open compartment into which the detergent composition is added. A second water-soluble film is then laid over the first film in such an orientation as to close the opening of the compartment. The first and second films are then sealed together along a seal region.

The unit dose article may comprise more than one compartment, even at least two compartments, or even at least three compartments. The compartments may be arranged in superposed orientation, i.e. one positioned on top of the other. In such an orientation the unit dose article will comprise three films, top, middle and bottom. Alternatively, the compartments may be positioned in a side-by-side orientation, i.e. one orientated next to the other. The compartments may even be orientated in a 'tyre and rim' arrangement, i.e. a first compartment is positioned next to a second compartment, but the first compartment at least partially surrounds the second compartment, but does not completely enclose the second compartment. Alternatively one compartment may be completely enclosed within another compartment.

Wherein the unit dose article comprises at least two compartments, one of the compartments may be smaller than the other compartment. Wherein the unit dose article comprises at least three compartments, two of the compartments may be smaller than the third compartment, and preferably the smaller compartments are superposed on the larger compartment. The superposed compartments preferably are orientated side-by-side.

In a multi-compartment orientation, the detergent composition according to the present invention may be comprised in at least one of the compartments. It may for example be comprised in just one compartment, or may be comprised in two compartments, or even in three compartments.

Each compartment may comprise the same or different compositions. The different compositions could all be in the same form, or they may be in different forms.

The water-soluble unit dose article may comprise at least two internal compartments, wherein the liquid laundry detergent composition is comprised in at least one of the compartments, preferably wherein the unit dose article comprises at least three compartments, wherein the detergent composition is comprised in at least one of the compartments.

FIG. 1 discloses a water-soluble unit dose article (1) according to the present invention. The water-soluble unit dose article (1) comprises a first water-soluble film (2) and a second water-soluble film (3) which are sealed together at a seal region (4). The liquid laundry detergent composition (5) is comprised within the water-soluble soluble unit dose article (1).

Water-Soluble Film

The film useful in the present invention is soluble or dispersible in water. The water-soluble film preferably has a thickness of from 20 to 150 micron, preferably 35 to 125 micron, even more preferably 50 to 110 micron, most preferably about 76 micron.

Preferably, the film has a water-solubility of at least 50%, preferably at least 75% or even at least 95%, as measured by the method set out here after using a glass-filter with a maximum pore size of 20 microns:

5 grams±0.1 gram of film material is added in a pre-weighed 3 L beaker and 2L±5 ml of distilled water is added. This is stirred vigorously on a magnetic stirrer, Labline model No. 1250 or equivalent and 5 cm magnetic stirrer, set at 600 rpm, for 30 minutes at 30° C. Then, the mixture is filtered through a folded qualitative sintered-glass filter with a pore size as defined above (max. 20 micron). The water is dried off from the collected filtrate by any conventional method, and the weight of the remaining material is determined (which is the dissolved or dispersed fraction). Then, the percentage solubility or dispersability can be calculated.

Preferred film materials are preferably polymeric materials. The film material can, for example, be obtained by casting, blow-moulding, extrusion or blown extrusion of the polymeric material, as known in the art.

Preferred polymers, copolymers or derivatives thereof suitable for use as pouch material are selected from polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatine, natural gums such as xanthum and carragum. More preferred polymers are selected from polyacrylates and water-soluble acrylate copolymers, methylcellulose, carboxymethylcellulose sodium, dextrin, ethylcellulose, hydroxyethyl cellulose, hydroxypropyl methylcellulose, maltodextrin, polymethacrylates, and most preferably selected from polyvinyl alcohols, polyvinyl alcohol copolymers and hydroxypropyl methyl cellulose (HPMC), and combinations thereof. Preferably, the level of polymer in the pouch material, for example a PVA polymer, is at least 60%. The polymer can have any weight average molecular weight, preferably from about 1000 to 1,000,000, more preferably from about 10,000 to 300,000 yet more preferably from about 20,000 to 150,000.

Preferably, the water-soluble film comprises polyvinyl alcohol polymer or copolymer, preferably a blend of polyvinylalcohol polymers and/or polyvinylalcohol copolymers, preferably selected from sulphonated and carboxylated anionic polyvinylalcohol copolymers especially carboxylated anionic polyvinylalcohol copolymers, most preferably a blend of a polyvinylalcohol homopolymer and a carboxylated anionic polyvinylalcohol copolymer.

Preferred films exhibit good dissolution in cold water, meaning unheated distilled water. Preferably such films exhibit good dissolution at temperatures of 24° C., even more preferably at 10° C. By good dissolution it is meant that the film exhibits water-solubility of at least 50%, preferably at least 75% or even at least 95%, as measured by the method set out here after using a glass-filter with a maximum pore size of 20 microns, described above.

Preferred films are those supplied by Monosol under the trade references M8630, M8900, M8779, M8310.

The film may be opaque, transparent or translucent. The film may comprise a printed area.

The area of print may be achieved using standard techniques, such as flexographic printing or inkjet printing.

The film may comprise an aversive agent, for example a bittering agent. Suitable bittering agents include, but are not limited to, naringin, sucrose octaacetate, quinine hydrochloride, denatonium benzoate, or mixtures thereof. Any suitable level of aversive agent may be used in the film. Suitable levels include, but are not limited to, 1 to 5000 ppm, or even 100 to 2500 ppm, or even 250 to 2000 rpm.

Detergent Composition

The water-soluble unit dose article comprises a detergent composition, preferably a liquid laundry detergent composition. The term 'liquid laundry detergent composition' refers to any laundry detergent composition comprising a liquid capable of wetting and treating a fabric, and includes, but is not limited to, liquids, gels, pastes, dispersions and the like. The liquid composition can include solids or gases in suitably subdivided form, but the liquid composition excludes forms which are non-fluid overall, such as tablets or granules.

Without wishing to be bound by theory, preferably the optionally encapsulated lipase variants are formulated into a liquid laundry detergent as this enables faster release into the wash liquor. This is especially beneficially in quick and cold wash cycles in which the risk of the being stuck in undissolved powder pasty phase is minimised.

The liquid detergent composition can be used in a fabric hand wash operation or may be used in an automatic machine fabric wash operation.

Detergent Adjunct

The detergent composition, preferably liquid laundry detergent composition, comprises a detergent adjunct, for example selected from surfactants, polymers, builders, dye transfer inhibiting agents, dispersants, enzymes, enzyme stabilizers, catalytic materials, bleach, bleach activators, hydrogen peroxide, sources of hydrogen peroxide, pre-formed peracids, polymeric dispersing agents, anti-redeposition agents, brighteners, suds suppressors, aesthetic dyes, hueing dyes, opacifiers, perfumes, perfume delivery systems, structurants, hydrotropes, processing aids, solvents, pigments, flocculating aid, chelating agents, and mixtures thereof.

The detergent adjunct preferably comprises a surfactant, in particular for a cleaning composition the surfactant preferably comprises anionic and/or nonionic surfactants, preferably in a weight ratio of from 50:1 to 1:10, or more preferably from 20:1 to 1:2.

The detergent composition preferably comprises up to 50%, preferably between 5% and 50%, more preferably between 7.5% and 45%, even more preferably between 10% and 40%, or even more preferably between 12% and 37%, most preferably between 15% and 30% by weight of the detergent composition of a non-soap anionic surfactant. Preferably, the non-soap anionic surfactant comprises linear alkylbenzene sulphonate, alkoxylated alkyl sulphate or a mixture thereof. More preferably, the non-soap anionic surfactant is a mixture of linear alkylbenzene sulphonate and alkoxylated alkyl sulphate, more preferably a mixture of linear alkylbenzene sulphonate and ethoxylated alkyl sulphate.

Preferably, the weight ratio of linear alkylbenzene sulphonate to alkoxylated alkyl sulphate, more preferably linear alkylbenzene sulphonate to ethoxylated alkyl sulphate is from 1:2 to 20:1, preferably from 1.1:1 to 15:1, more preferably from 1.2:1 to 10:1, even more preferably from 1.3:1 to 5:1, most preferably from 1.4:1 to 3:1.

The weight ratio of linear alkylbenzene sulphonate to ethoxylated alkyl sulphate may be from 1:10 to 20:1, preferably from 1:7 to 3:1, more preferably from 1:5 to 1.5:1.

Preferably, the weight ratio of total anionic surfactant (i.e. all anionic surfactant present in the liquid composition): non-ionic surfactant in the liquid composition is between 5:1 and 23:1. Preferably, the non-soap anionic surfactant is neutralised with an amine, preferably selected from monoethanolamine, diethanolamine, triethanolamine or a mixture thereof, more preferably monoethanolamine.

The detergent composition preferably comprises between 0% and 40%, preferably between 0.01% and 30%, more preferably between 0.1% and 20%, most preferably between 0.15% and 15% by weight of the liquid laundry detergent composition of a non-ionic surfactant. Preferably, the non-ionic surfactant is selected from alcohol alkoxylates, an oxo-synthesised alcohol alkoxylate, Guerbet alcohol alkoxylates, alkyl phenol alcohol alkoxylates or a mixture thereof.

Preferably, the detergent composition comprises between 1.5% and 20%, more preferably between 2% and 15%, even more preferably between 3% and 10%, most preferably between 4% and 8% by weight of the liquid detergent composition of soap, preferably a fatty acid salt, more preferably an amine neutralized fatty acid salt, wherein preferably the amine is an alkanolamine more preferably selected from monoethanolamine, diethanolamine, triethanolamine or a mixture thereof, more preferably monoethanolamine.

The detergent composition preferably comprises a cationic polysaccharide, preferably selected from cationically modified hydroxyethyl cellulose, cationically modified hydroxypropyl cellulose, cationically and hydrophobically modified hydroxyethyl cellulose, cationically and hydrophobically modified hydroxypropyl cellulose, or a mixture thereof, more preferably cationically modified hydroxyethyl cellulose, cationically and hydrophobically modified hydroxyethyl cellulose, or a mixture thereof. The cationic polysaccharide preferably is present between 0.05% and 3%, preferably between 0.1% and 2%, more preferably between 0.2% and 1%, most preferably between 0.25% and 0.75% by weight of the liquid laundry detergent composition.

Preferably, the detergent composition comprises an alkoxylated polyethyleneimine, preferably an ethoxylated polyethyleneimine. Preferably, the liquid laundry detergent composition comprises between 0.1% and 10%, preferably between 0.5% and 7%, more preferably between 1% and 5% by weight of the liquid laundry detergent composition of the ethoxylated polyethyleneimine.

The water-soluble unit dose article preferably comprises 20% or less, or more preferably 15% or less by weight of the unit dose article of water, preferably comprising between 0.1% and 15%, more preferably between 1% and 12.5% by weight of the unit dose article of water.

Preferably, the water-soluble unit dose article comprises between 10% and 60%, preferably between 12% and 50%, most preferably between 15% and 40% by weight of the liquid laundry detergent composition of a non-aqueous solvent, preferably wherein the non-aqueous solvent is selected from 1,2-Propanediol, glycerol, sorbitol, dipropylene glycol, tripropyleneglycol, or a mixture thereof.

Enzymes—

The composition may comprise one or more enzymes, optionally encapsulated in microcapsules as described herein, which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, mannanases, pectate lyases, keratinases, reductases, oxidases, phenoloxidases, lipoxygenases, ligninases, pullulanases, tannases, pentosanases, malanases, β-glucanases, arabinosidases, hyaluronidase, chondroitinase, laccase, chlorophyllases, amylases, or mixtures thereof. A typical combination is an enzyme cocktail that may comprise e.g. a protease and lipase in conjunction with amylase. When present in a composition, the aforementioned additional enzymes may be present at levels from 0.00001 to 2 wt %, from 0.0001 to 1 wt % or from 0.001 to 0.5 wt % enzyme protein by weight of the composition.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

The lipase variant may optionally be encapsulated in a microcapsule. In addition, the detergent composition of the invention may further comprise one or more additional enzymes in encapsulated form. Examples of suitable enzymes are selected from the group consisting of protease, amylase, additional lipase, cellulase, mannanase, pectinase, DNAse, laccase, peroxidase, haloperoxidase, perhydrolase, and combinations thereof.

The enzyme(s) in the composition may include one or more enzymes suitable for including in laundry or dishwashing detergent (detergent enzymes) such as a protease (e.g., subtilisin or metalloprotease), lipase, cutinase, amylase, carbohydrase, cellulase, pectinase, mannanase, arabinase, galactanase, xanthanase, xylanase, DNAse, perhydrolase, oxidoreductase (e.g., laccase, peroxidase, peroxygenase and/or haloperoxidase). Preferred detergent enzymes are protease (e.g., subtilisin or metalloprotease), lipase, amylase, lyase, cellulase, pectinase, mannanase, DNAse, perhydrolase, and oxidoreductases (e.g., laccase, peroxidase, peroxygenase and/or haloperoxidase); or combinations thereof. More preferred detergent enzymes are protease (e.g., subtilisin or metalloprotease), lipase, amylase, cellulase, pectinase, and mannanase; or combinations thereof.

The composition or microcapsule composition may include more than 0.1% (w/w) active enzyme protein, in particular lipase variant of the invention; preferably more than 0.25%, more preferably more than 0.5%, more preferably more than 1%, more preferably more than 2.5%, more preferably more than 5%, more preferably more than 7.5%, more preferably more than 10%, more preferably more than 12.5%, more preferably more than 15%, even more preferably more than 20%, and most preferably more than 25% (w/w) active enzyme protein.

In one aspect preferred enzymes would include a cellulase. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO89/09259.

Especially suitable cellulases are the alkaline or neutral cellulases having colour care benefits. Examples of such cellulases are cellulases described in EP0495257, EP0531372, WO96/11262, WO96/29397, WO98/08940. Other examples are cellulase variants such as those described in WO94/07998, EP0531315, U.S. Pat. Nos. 5,457,046, 5,686,593, 5,763,254, WO95/24471, WO98/12307 and PCT/DK98/00299.

Commercially available cellulases include Celluzyme™, and Carezyme™ (Novozymes A/S), Clazinase™, and Puradax HA™ (Genencor International Inc.), and KAC-500 (B)™ (Kao Corporation).

In one aspect preferred enzymes would include a protease. Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the 51 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin *lentus*, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from Cellumonas described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V4I, S9R, A15T, K27R, *36D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names Alcalase®, Blaze®; Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Neutrase®, Everlase® and Esperase® all could be sold as Ultra® or Evity® (Novozymes A/S), those sold under the tradename Maxatase®, Maxacal®, Maxapem®, Purafect®, Purafect Prime®, Preferenz™, Purafect MA®, Purafect Ox®, Purafect OxP®, Puramax®, Properase®, Effectenz™, FN2®, FN3®, FN4®, Excellase®, Opticlean® and Optimase® (Danisco/DuPont), Axapem™ (Gist-Brocases N.V.), BLAP® and variants hereof (Henkel AG) and KAP (*Bacillus alkalophilus* subtilisin) from Kao.

In one aspect preferred enzymes would include an amylase. Suitable amylases may be an alpha-amylase or a glucoamylase and may be of bacterial or fungal origin. Chemically modified or protein engineered mutants are included. Suitable amylases include, for example, commercially available amylases such as Duramyl™, Termamyl™, Termamyl Ultra™, Fungamyl™, Ban™, Stainzyme™, Stainzyme Plus™, Amplify®, Supramyl™, Natalase™, Liquozyme X and BAN™ (from Novozymes A/S), KEMZYM® AT 9000 Biozym Biotech Trading GmbH Wehlistrasse 27b A-1200 Wien Austria, and Rapidase™, Purastar™/Effectenz™, Powerase, Preferenz 5100, Preferenx 5110, ENZYSIZE®, OPTISIZE HT PLUS®, and PURASTAR OXAM® (Danisco/DuPont) and KAM® (Kao).

Suitable additional lipases and cutinases include those of bacterial or fungal origin. Chemically modified or protein engineered mutant enzymes are included. Examples include lipase from *Thermomyces*, e.g. from *T. lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), P. sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412, WO13/033318), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™; Lipolase Ultra™; Lipex Evity 100L; Lecitase™; Lipoprime™ and Lipoclean™ (Novozymes A/S), Lumafast (originally from Genencor) and Lipomax (originally from Gist-Brocades) and *Bacillus* sp. from Solvay.

Still other examples are lipases sometimes referred to as acyltransferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

In one aspect, other preferred enzymes include microbial-derived endoglucanases exhibiting endo-beta-1,4-glucanase activity (EC3.2.1.4), including a bacterial polypeptide endogenous to a member of the genus *Bacillus*. Suitable endoglucanases are sold under the tradenames Celluclean® and Whitezyme® (Novozymes).

Other preferred enzymes include pectate lyases sold under the tradenames Pectawash®, Pectaway®, Xpect® and mannanases sold under the tradenames Mannaway® (Novozymes), and Purabrite® (Danisco/DuPont).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP238216.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Polymers

Preferably the detergent adjunct comprises a polymer or mixture of polymers. The detergent composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fibre protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate.

Examples of builders include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycine-N,N-diacetic acid (MGDA), glutamic acid-N,N-diacetic acid (GLDA), 1-hydroxyethane-1,1-diphosphonic acid, N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(sulfomethyl)aspartic acid (SMAS), N-(2-sulfoethyl)-aspartic acid (SEAS), N-(sulfomethylglutamic acid (SMGL), N-(2-sulfoethyl)-glutamic acid (SEGL), N-methyliminodiacetic acid (MIDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and N'-(2-hydroxyethyl)ethylenediamine-N,N,N'-triacetic acid (HEDTA), diethanolglycine (DEG), and combinations and salts thereof. Phosphonates suitable for use herein include 1-hydroxyethane-1,1-diphosphonic acid (HEDP), ethylenediaminetetrakis (methylenephosphonicacid) (EDTMPA), diethylenetriaminepentakis (methylenephosphonic acid) (DTMPA or DTPMPA or DTPMP), nitrilotris (methylenephosphonic acid) (ATMP or NTMP), 2-phosphonobutane-1,2,4-tricarboxylic acid (PBTC), hexamethylenediaminetetrakis (methylenephosphonic acid) (HDTMP).

The composition may also contain 0-50% by weight, such as about 5% to about 30%, of a detergent co-builder. Non-limiting examples of co-builders include homopolymers of polyacrylates or copolymers thereof, such as poly (acrylic acid) (PAA) or copoly (acrylic acid/maleic acid) (PAA/PMA) or polyaspartic acid.

Fabric Hueing Agents

The detergent composition of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO 2005/03274, WO 2005/03275, WO 2005/03276 and EP 1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO 2007/087243.

Dispersants

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The cleaning compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent composition may preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho [1,2-d][1,2,3]triazol-2-yl)-2-[(E)-2-phenylvinyl]benzenesulfonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Tinopal CBS-X is a 4.4'-bis-(sulfostyryl)-biphenyl disodium salt also known as Disodium Distyrylbiphenyl Disulfonate. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc.

Preferably the detergent adjunct comprises a polyester terephthalate. Preferably, the polyester terephthalate comprises a backbone grafted with one or more anionic groups, more preferably, comprising an anionic polyester of propylene terephtalate.

Suitable anionic polyesters are those that are derived from terephtalic acid, 5-sulfoisophtalic acid or the salt of 5-sulfoisophtalic acid, from ethylene glycol or polyethylene glycol, propylene glycol or polypropylene glycol and polyalkyleneglycol monoalkyl ether, and optionally from further additional monomers.

Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers. Suitable graft co-polymers are described in more detail in WO 2007/138054, WO 2006/108856 and WO 2006/113314 (hereby incorporated by reference).

Preferably the detergent adjunct comprises an amphiphilic graft polymer, preferably based on polyalkylene oxides and vinyl esters, preferably based on water-soluble polyalkylene oxides as a graft base and side chains formed by polymerization of a vinyl ester component, said polymer having an average of <1 graft site per 50 alkylene oxide units, more preferably wherein the molar ratio of grafted to ungrafted alkylene oxide units is from 0.002 to 0.05, preferably from 0.002 to 0.035, more preferably from 0.003 to 0.025, most preferably from 0.004 to 0.02. Preferred graft polymers have a mean molecular mass Mw of from 3000 to 100 000. Preferred polymers comprise from 20% to 70%, preferably from 25% to 60% by weight of the polymer of the polyalkylene oxide, preferably the water-soluble polyalkylene oxide as a graft base. Preferably, the polyalkylene oxide graft base is a polyethylene glycol.

Preferably, the polymer comprises from 30% to 80% by weight of the vinyl ester component preferably wherein the vinyl ester component comprises a vinyl acetate, vinyl propionate or a mixture thereof, and optionally a C1-C8-alkyl acrylate more preferably from 70% to 100% by weight of vinyl acetate and from 0% to 30% by weight of a C1-C8-alkyl acrylate.

Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof. Preferably the detergent adjunct comprises a carboxymethylcellulose or derivative thereof, preferably selected from carboxymethyl cellulose, hydrophobically modified carboxymethyl celluloses or a mixture thereof, hydrophobically modified carboxymethylcellulose are particularly preferred.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Rheology Modifiers

The detergent compositions of the present invention may also include one or more rheology modifiers, structurants or thickeners, as distinct from viscosity reducing agents. The rheology modifiers are selected from the group consisting of non-polymeric crystalline, hydroxy-functional materials, polymeric rheology modifiers which impart shear thinning characteristics to the aqueous liquid matrix of a liquid detergent composition. The rheology and viscosity of the detergent can be modified and adjusted by methods known in the art, for example as shown in EP 2169040.

Other suitable adjunctls include, but are not limited to, anti-shrink agents, anti-wrinkling agents, bactericides, binders, carriers, dyes, enzyme stabilizers, fabric softeners, fillers, foam regulators, hydrotropes, perfumes, pigments, suds suppressors, solvents, and structurants for liquid detergents and/or structure elasticizing agents.

Process of Making

Those skilled in the art will know how to make the water-soluble unit dose article and liquid laundry detergent composition of the present invention using commonly known manufacturing techniques.

Process for Washing

A further aspect of the present invention is a process for washing fabrics comprising the steps of;
 a. Combining a water-soluble unit dose article according to the present invention with sufficient water to dissolve the water-soluble film and dilute the laundry detergent composition, preferably by a factor of between 300 and 3000 fold, preferably between 300 and 800 fold to form a wash liquor;
 b. Combining the wash liquor with at least one fabric to be washed.

Enzyme Stabilizers and/or Rheology Modifiers

The compositions of the invention preferably comprise enzyme stabilizers, for example, polyols, polymers, reversible enzyme inhibitors, divalent cations, enzyme substrates, antioxidants etc. Water soluble stabilizers are preferred.

Addition of slowly dissolving stabilizers can be used to create a local environment inside the capsule, which is more "friendly" to the encapsulated enzyme/compound, thus improving the stability during storage.

Examples of reversible protease inhibitors are boronic acids, peptide aldehydes and derivatives hereof and high molecular protein-type inhibitors (like BASI/RASI inhibitors, see WO 2009/095425). An example of metalloprotease inhibitors is described in WO 2008/134343. Protease inhibitors are described in more detail below under the heading "Protease Inhibitors".

Stabilizing polymers can be based on, e.g., polyvinylypyrrolidon, polyvinylacetate, polyvinylalcohol and copolymers hereof. Stabilizing polyols can be smaller molecules like glycerol, sorbitol, propylene glycol etc. but also larger molecules like polyethylene glycol, polysaccharides etc.

Of stabilizing divalent cations Ca2+, Mg2+ and Zn2+ are well-known in the art. Thus, in an embodiment, the composition of the invention comprise a source of Ca2+, Mg2+ or Zn2+ ions. Preferably, the source of Ca2+, Mg2+ or Zn2+ ions is a poorly soluble (slowly dissolving) salt of Ca2+, Mg2+ or Zn2+. Poorly soluble means that the solubility in pure water at 20° C. is less than 5 g/l, 2 g/l, 1 g/l, 0.5 g/l, 0.2 g/l, 0.1 g/l, or 0.05 g/1. Preferred salts of Ca2+, Mg2+ or Zn2+ are calcium carbonate, magnesium carbonate, zinc carbonate, calcium sulfate, calcium sulfite, magnesium sulfite, zinc sulfite, calcium phosphate, dicalcium phosphate, magnesium phosphate, zinc phosphate, calcium citrate, magnesium citrate, zinc citrate, calcium oxalate, magnesium oxalate, zinc oxalate, calcium tartrate, magnesium tartrate, or zinc tartrate.

Also, slowly dissolving acids or bases can be used to create a local pH inside the microcapsule, which is more "friendly" to the encapsulated enzyme/compound.

Enzymes are in most cases stabilized by addition of their substrates (e.g., protein for proteases, starch for amylases etc.). Antioxidants or reducing agents can be applied to reduce oxidation of enzymes, e.g., thiosulfate, ascorbate etc. The net dosage needed of these stabilizers per gram detergent is much lower compared to adding the stabilizers to the continuous detergent phase, as they are concentrated in the internal capsule phase, and will in many cases either not diffuse out during storage, or only slowly diffuse out depending on the structure and molecular weight of the stabilizer. Especially high molecular weight stabilizers (e.g., higher than 1 kDa, or higher than 2 kDa more preferred higher than 5 kDa) will give improved net efficiency. High molecular weight inhibitors, polymers, polyols, cations, enzyme substrates and antioxidants are thus preferred.

The enzyme may be protected by addition of a "scavenger" protein. Components destabilizing enzyme by reacting onto amino acid groups (e.g., amines) on the protein may thus react with the scavenger or sacrificial protein added. Scavenger protein with a sufficient large molecular weight to stay inside the capsules are preferred.

Enzyme stability may optionally be improved by adding a rheology modifying component thereby increasing viscosity of the internal capsule phase. An increased internal viscosity will slow down diffusion of enzyme destabilizers into the capsules (and/or slow down the diffusion of enzyme stabilizers out of the capsule) and thus prolong the lifetime of the enzyme. Examples of such viscosity modifiers are polymers like polyethylene glycol (PEG), polyethylene oxide (PEO), hydrophilic polyurethane, polyvinylpyrrolidon (PVP) and PVP vinyl acetate copolymers, starch, hyaluronic acid, water soluble cellulose derivatives like carboxymethyl cellulose, water soluble gums like gum Arabic, locust bean gum, guar gum or xanthan gum etc. and combinations or copolymers hereof. Most preferred are nonionic high molecular weight polymers, with a molecular weight higher than 1 kDa, or higher than 2 kDa, more preferred higher than 5 kDa. Nonionic polymers are preferred as they in most cases are more compatible with the reactive membrane polymer than ionic polymers.

The high viscosity may be accomplished by producing the capsules using a high viscosity aqueous phase, or—more sophisticated—producing capsules where the viscosity increase first occur after producing the emulsion/capsules. This "triggered" viscosity increase is preferable as preparing emulsions with a high viscosity aqueous phase can be difficult. Triggered viscosity increase can be done in situ when added to detergent by the internal capsule phase having a higher water activity than the detergent to which it is added, thus water will diffuse out of the capsules (but not the rheology modifier) increasing the viscosity of the internal phase after addition to detergent. This can also be utilized using diffusion of salt or other low molecular components, e.g., by having a component that will increase viscosity when salt concentration is reduced by addition to detergent (e.g., a polymer that is precipitated at the initial high salt content but soluble when salt concentration is reduced due to diffusion of salt when added to detergent). Another way to trigger viscosity is to use components where the viscosity is dependent on the pH. For some interfacial polymerization processes (e.g., amine—acid halogen reaction) the pH of the internal phase will change during encapsulation, in the case of amine-acid halogen pH will be reduced during the interfacial polymerization. This can be used to trigger an increase in viscosity. Many rheology modifiers like polyacrylates show a viscosity maximum at a specific pH or pH range. Carbopol 934 from Lubrizol and Texipol 63-258 from Scott-Bader are examples of rheology modifiers where viscosity is significantly increased when reducing the pH from 11 to 8, or increasing pH from 4 to 8. Another polymer type with a different viscosity at low pH and at high pH is partially hydrolyzed polyacrylamide. Yet another possibility is to use rheology modifiers which are temperature dependent, thus making the emulsion/encapsulation at one temperature, and subsequently changing the temperature to increase viscosity. Also a light or ultrasound induced viscosity can be utilized. Yet another method is to use shear-thinning rheology modifiers, such that the viscosity is low at high shear when the emulsion is formed and high when shear is reduced.

Another stabilization technique when the enzyme are encapsulated is to assure that the enzyme is precipitated in the capsules during storage, for example by addition of precipitants like salt or polyethylene glycol (PEG). The same "triggered stabilization" as described above can be used, e.g., by addition of PEG, which after addition to detergent is concentrated by water diffusing out to a degree where the enzyme will precipitate. In this way the enzyme can be in solution during processing of the capsules, but precipitated when added to detergent.

Enzymes can also be used in precipitated or crystal form when preparing the microcapsules.

The present invention is further described by the following examples that should not be construed as limiting the scope of the invention.

EXAMPLES

Example 1: p-Nitrophenyl (pNP) Assay

The hydrolytic activity of a lipase may be determined by a kinetic assay using p-nitrophenyl acyl esters as substrate.

A 100 mM stock solution in DMSO for each of the substrates p-nitrophenyl butyrate (C4), p-nitrophenyl caproate (C6), p-nitrophenyl caprate (C10), p-nitrophenyl laurate (C12) and p-nitrophenyl palmitate (C16) (all from Sigma-Aldrich Danmark A/S, Kirkebjerg Allé 84, 2605 Brøndby; Cat. no.: C3:N-9876, C6: N-0502, C10: N-0252, C12: N-2002, C16: N-2752) is diluted to a final concentration of 1 mM 25 mM in the assay buffer (50 mM Tris; pH 7.7; 0.4% Triton X-100).

The lipase variants, the parent lipase and appropriate controls, e.g., Lipolase™ (SEQ ID NO: 2) in 50 mM Hepes; pH 8.0; 10 ppm Triton X-100; +/−20 mM $CaCl_2$) are added to the substrate solution in the following final protein concentrations: 0.01 mg/ml; $5\times10^{-3}$ mg/ml; $2.5\times10^4$ mg/ml; and $1.25\times10^4$ mg/ml in 96-well NUNC plates (Cat. No. 260836, Kamstrupvej 90, DK-4000, Roskilde). The buffer is also run as a negative control. Release of p-nitrophenol by hydrolysis of a p-nitrophenyl acyl may be monitored at 405 nm for 5 minutes in 10 second intervals on a Spectra max 190 (Molecular Devices GmbH, Bismarckring 39, 88400 Biberach an der Riss, GERMANY). The hydrolytic activity towards one or more substrates of a variant may be compared to that of the parent lipase.

Example 2: Construction of Variants by Site-Directed Mutagenesis

Site-directed variants were constructed of the *Thermomyces lanuginosus* lipase (TLL) (SEQ ID NO: 2). The variants were made by traditional cloning of DNA fragments (Sambrook et al., Molecular Cloning: A Laboratory Manual, 2nd Ed., Cold Spring Harbor, 1989) using PCR together with properly designed mutagenic oligonucleotides that introduced the desired mutations in the resulting sequence.

Mutagenic oligos were designed corresponding to the DNA sequence flanking the desired site(s) of mutation, separated by the DNA base pairs defining the insertions/deletions/substitutions, and purchased from an oligo vendor such as Life Technologies.

In order to test the TLL variants, the mutated DNA encoding a variant was integrated into a competent *A. oryzae* strain by homologous recombination, fermented using standard protocols (yeast extract based media, 3-4 days, 30° C.), and purified by chromatography. In this manner, the variants listed in the Table below were constructed and produced.

| Variants of SEQ ID NO 2 |
| --- |
| G23S + D27N + F51I + E56R + R118F + T231R + N233R + P256T |
| A40I + F51L + E56R + D57N + K98I + R118F + G163S + T231R + N233R + P256T |
| G23S + D27N + A40I + F51I + E56R + R118F + T231R + N233R + T244E + P256T |
| D27N + F51I + E56R + R118F + T231R + N233R + T244E |
| G23S + D27N + F51I + E56R + K98I + R118F + Y220F + T231R + N233R + T244E + P256T |

Example 3: Relative Wash Performance (RP(Wash))

Washing experiments were performed using Automatic Mechanical Stress Assay (AMSA) in order to assess the wash performance in laundry. The AMSA plate has a number of slots for test solutions and a lid firmly squeezing the laundry sample, the textile to be washed against all the slot openings. During the washing time, the plate, test solutions, textile and lid are vigorously shaken to bring the test solution in contact with the textile and apply mechanical stress in a regular, periodic oscillating manner. For further description see WO02/42740 especially the paragraph "Special method embodiments" at page 23-24.

The laundry experiments were conducted under the experimental conditions specified below:

Detergent: 3.3 g/L Detergent B or 0.8 g/L Detergent J

Test solution volume: 160 µL

Wash time: 20 minutes

Temperature: 30° C.

Lipase dosage: 0 ppm or 0.35 ppm

Test material: Cream Annatto stained EMPA221 cotton textile prepared as described in WO06/125437 except to exchanging turmeric with annatto (Annatto: A-320-WS, Chr. Hansen A/S, Boege Alle' 10-12, DK-2970, Hoersholm, Denmark & EMPA221: EMPA, Lerchenfeldstrasse 5, CH-9014, St. Gallen, Switzerland)

Water hardness was adjusted to 15° dH or 6° dH by addition of $CaCl_2$, $MgCl_2$ and $NaHCO_3$ ($Ca^{2+}$:$Mg^{2+}$: $HCO_3^-$=4:1:7.5 or 2:1:4.5).

TABLE 1

| Composition Detergent A (wt %) | |
| --- | --- |
| NaOH, pellets (>99%) | 1.05 |
| Linear alkylbenzenesulfonic acid (LAS) (97%) | 7.20 |
| Sodium laureth sulfate (SLES) (28%) | 10.58 |
| Soy fatty acid (>90%) | 2.75 |
| Coco fatty acid (>99%) | 2.75 |
| Alcohol ethoxylate (AEO) with 8 mol EO; Lutensol TO 8 (~100%) | 6.60 |
| Triethanol amine (100%) | 3.33 |
| Na-citrate, dihydrate (100%) | 2.00 |
| DTMPA; diethylenetriaminepentakis(methylene)pentakis(phosphonic acid), heptasodium salt (Dequest 2066 C) (~42% as Na7 salt) | 0.48 |
| MPG (>98%) | 6.00 |
| EtOH, propan-2-ol (90/10%) | 3.00 |
| Glycerol (>99.5%) | 1.71 |
| Sodium formate (>95%) | 1.00 |
| PCA (40% as sodium salt) | 0.46 |
| Water up to | 100 |

TABLE 2

| Composition Detergent B (wt %) | |
| --- | --- |
| sodium hydroxide (>99%) | 0.50 |
| Linear alkylbenzenesulfonic acid (LAS) (97%) | 5.00 |
| sodium alkyl sulfate (90%) | 5.00 |
| AEOS, sodium (C12) alkyl ether sulfate (70.5%) | 10.00 |
| Coco fatty acid (>99%) | 1.00 |
| Alcohol ethoxylate (AEO) with 7 mol EO (99.5%) | 5.00 |
| MEA, monoethanolamine (99.5%) | 0.20 |
| MPG (>98%) | 3.00 |
| EtOH, propan-2-ol (90/10%) | 1.50 |
| DTPA, diethylenetriaminepentaacetic acid, pentasodium salt, (~40% as Na5 salt) | 0.10 |
| sodium citrate (>99%) | 4.00 |
| sodium formate (>99%) | 1.00 |
| Water up to | 100 |

After washing the textiles were flushed in tap water and excess water was removed from the textiles using filter paper and immediately thereafter the textiles were dried at 100° C. for 15 minutes.

The wash performance was measured as the color change of the washed soiled textile. The soil was cream mixed with annatto. Annatto contains the colorant norbixin, which functions as a pH indicator with a pH dependent color change. Lipase activity leads to release of free fatty acids from the cream acylglycerols and this leads to pH decrease and thereby color change of the norbixin pH indicator. Lipase wash performance can therefore be expressed as the extent of color change of light reflected-emitted from the washed soiled textile when illuminated with white light.

Color measurements were made with a professional flatbed scanner (EPSON EXPRESSION 11000XL, Atea A/S, Lautrupvang 6, 2750 Ballerup, Denmark), which was used to capture an image of the washed soiled textile. To extract a value for the light intensity from the scanned images, 24-bit pixel values from the image were converted into values for red, green and blue (RGB).

Color change due to lipase activity was measured as the change in the reflection-emitting of green light (G) relative to the light intensity value (Int) calculated as:

$$Int = \sqrt{R^2 + G^2 + B^2}$$

The relative wash performance (RP(Wash)) of a lipase relative to a reference lipase was calculated as:

$$RP(Wash) = (G/Int(\text{tested lipase}) - G/Int(\textit{no enzyme})) / (G/Int(\text{lipase ref.}) - G/Int(\textit{no enzyme})).$$

A lipase is considered to exhibit improved wash performance, if it performs better than the reference (RP(Wash) >1). In the context of the present invention the reference enzyme is the lipase shown as SEQ ID NO: 2.

Odor Detection by Solid Phase Micro Extraction Gas Chromatograph Measurements

The butyric acid release (odor) from the lipase washed swatches were measured by Solid Phase Micro Extraction Gas Chromatography (SPME-GC) using the following method.

Cream Annatto stained EMPA221 cotton textile was washed as specified above and after wash, excess water was removed from the textile using filter paper and the textile was thereafter dried at 25° C. for 2 hours. Each SPME-GC measurement was performed with four pieces of the washed and dried textile (5 mm in diameter), which were transferred to a Gas Chromatograph (GC) vial and the vial was closed. The samples were incubated at 30° C. for 24 hours and subsequently heated to 140° C. for 30 minutes and stored at 20° C.-25° C. for at least 4 hours before analysis. The analyses were performed on a Varian 3800 GC equipped with a Stabilwax-DA w/Integra-Guard column (30 m, 0.32 mm ID and 0.25 micro-m df) and a Carboxen PDMS SPME fiber (85 micro-m). Sampling from each GC vial was done at 50° C. for 8 minutes with the SPME fiber in the headspace over the textile pieces and the sampled compounds were subsequently injected onto the column (injector temperature=250° C.). Column flow=2 ml helium/minute. Column oven temperature gradient: 0 minute=50° C., 2 minutes=50° C., 6 minutes 45 seconds=240° C., 11 minutes 45 seconds=240° C. Detection was done using a Flame Ionization Detector (FID) and the retention time for butyric acid was identified using an authentic standard.

The relative odor release (RP(Odor)) of a lipase is the ratio between the amount butyric acid released (peak area) from a lipase washed swatch and the amount butyric acid released (peak area) from a reference lipase washed swatch, after both values have been corrected for the amount of butyric acid released (peak area) from a non-lipase washed swatch (blank). The relative odor performance (RP(Odor)) of the polypeptide is calculated in accordance with the below formula:

RP(Odor)=(odor(tested lipase)−odor(no enzyme))/(odor(lipase ref.)−odor(no enzyme))

Where odor is the measured butyric acid (peak area) released from the textile surface.
Benefit Risk Factor (RP(Wash)/RP(Odor))

The Benefit Risk factor (BRF) describing the wash performance (Benefit) compared to the odor release (Risk) can be defined as RP(Wash)/RP(Odor). If the Benefit Risk factor of a lipase is higher than 1, the lipase has better wash performance relative to the released odor compared to the reference lipase (SEQ ID NO: 2).

Fluorescence was monitored every 20 seconds using in-built LED blue light for excitation and ROX-filter (610 nm, emission). Tm-values were calculated as the maximum value of the first derivative (dF/dK) (Gregory et al., 2009, J. Biomol. Screen. 14: 700).

| Construct Protein Mutations | Tm (° C.) |
|---|---|
| SEQ ID NO: 1 | 74.7 |
| G23S + D27N + F51I + E56R + R118F + T231R + N233R + P256T | 78.3 |
| A40I + F51L + E56R + D57N + K98I + R118F + G163S + T231R + N233R + P256T | 78.8 |
| G23S + D27N + A40I + F51I + E56R + R118F + T231R + N233R + T244E + P256T | 81.0 |
| D27N + F51I + E56R + R118F + T231R + N233R + T244E | 76.4 |
| G23S + D27N + F51I + E56R + K98I + R118F + Y220F + T231R + N233R + T244E + P256T | 77.7 |

Example 5: Construction of Variants by Site-Directed Mutagenensis

Site-directed variants were constructed of the *Thermomyces lanuginosus* lipase (TLL) (SEQ ID NO: 2). The variants were made by traditional cloning of DNA fragments (Sambrook et al., Molecular Cloning: A Laboratory Manual, 2nd Ed., Cold Spring Harbor, 1989) using PCR together with properly designed mutagenic oligonucleotides that introduced the desired mutations in the resulting sequence.

Mutagenic oligos were designed corresponding to the DNA sequence flanking the desired site(s) of mutation, separated by the DNA base pairs defining the insertions/deletions/substitutions, and purchased from an oligo vendor

| Construct Protein Mutations | AMSA Detergent B RP(Wash) 6° dH, 0.8 g/L | AMSA Detergent A RP(Wash) 6° dH, 3.3 g/L | AMSA Detergent A RP(Wash) 15° dH, 3.3 g/L | AMSA Detergent B RP(6° dH, 0.8 g/L) (odor) | AMSA Detergent B BRF |
|---|---|---|---|---|---|
| SEQ ID NO: 2 | 1.00 | 1.00 | 1.00 | 1.00 | 1.00 |
| G23S + D27N + F51I + E56R + R118F + T231R + N233R + P256T | 6.88 | 2.79 | 1.41 | 3.97 | 1.74 |
| A40I + F51L + E56R + D57N + K98I + R118F + G163S + T231R + N233R + P256T | 3.02 | 1.84 | 1.23 | 2.79 | 1.08 |
| G23S + D27N + A40I + F51I + E56R + R118F + T231R + N233R + T244E + P256T | 1.55 | 1.78 | 1.19 | 2.84 | 0.55 |
| D27N + F51I + E56R + R118F + T231R + N233R + T244E | 2.00 | 1.58 | 1.25 | 2.51 | 0.79 |
| G23S + D27N + F51I + E56R + K98I + R118F + Y220F + T231R + N233R + T244E + P256T | 2.80 | 1.72 | 1.30 | 2.41 | 1.16 |

Example 4: Protein Thermal Unfolding Analysis (TSA, Thermal Shift Assay)

Protein thermal unfolding of variants of SEQ ID NO: 1 was monitored with Sypro Orange (Invitrogen, S-6650) using a real-time PCR instrument (Applied Biosystems; Step-One-Plus).

In a 96-well white PCR-plate, 15 µl sample (purified enzyme diluted in 100 mM EPPS, 0.01% Troton-X-100; pH8.0) was mixed (1:1) with Sypro Orange (Conc.=10×; stock solution from supplier=5000×) in water.

The plate was sealed with an optical PCR seal. The PCR instrument was set at a scan-rate of 76° C. per hour, starting at 25° C. and finishing at 96° C.

such as Life Technologies. In order to test the TLL variants, the mutated DNA encoding a variant was integrated into a competent *A. oryzae* strain by homologous recombination, fermented using standard protocols (yeast extract based media, 3-4 days, 30° C.), and purified by chromatography. In this manner, the variants listed in the Table below were constructed and produced.

| Variants of SEQ ID NO: 2 |
|---|
| G23S + T231R + N233R |
| D27N + T231R + N233R |

-continued

| Variants of SEQ ID NO: 2 |
| --- |
| A40I + T231R + N233R |
| F51I + T231R + N233R |
| F51L + T231R + N233R |
| E56R + T231R + N233R |
| D57N + T231R + N233R |
| V60E + T231R + N233R |
| V60K + T231R + N233R |
| K98I + T231R + N233R |
| N101D + T231R + N233R |
| R118F + T231R + N233R |
| G163S + T231R + N233R |
| Y220F + T231R + N233R |
| T231R + N233R + T244E |
| T231R + N233R + P256T |
| E56R + R118F + T231R + N233R |
| R118F + T231R + N233R + P256T |
| A40I + R118F + T231R + N233R |
| F51I + E56R + R118F + T231R + N233R |
| F51L + E56R + R118F + T231R + N233R |
| E56R + D57N + R118F + T231R + N233R |
| E56R + V60K + R118F + T231R + N233R |
| G23S + D27N + F51I + E56R + V60E + R118F + T231R + N233R + P256T |
| G23S + D27N + A40I + F51I + E56R + K98I + N101D + R118F + T231R + N233R + T244E + P256T |
| G23S + D27N + A40I + F51I + E56R + V60K + R118F + T231R + N233R + T244E + P256T |

Example 6: Relative Wash Performance (RP(Wash))

Washing experiments were performed using Automatic Mechanical Stress Assay (AMSA) in order to assess the wash performance in laundry. The AMSA plate has a number of slots for test solutions and a lid firmly squeezing the laundry sample, the textile to be washed against all the slot openings. During the washing time, the plate, test solutions, textile and lid are vigorously shaken to bring the test solution in contact with the textile and apply mechanical stress in a regular, periodic oscillating manner. For further description see WO 02/42740 especially the paragraph "Special method embodiments" at page 23-24. The laundry experiments were conducted under the experimental conditions specified below:

Detergent: 3.3 g/L Detergent A or 0.8 g/L Detergent B
Test solution volume: 160 μL
Wash time: 20 minutes
Temperature: 30° C.
Lipase dosage: 0 ppm or 0.35 ppm
Test material: Cream Annatto stained EMPA221 cotton textile prepared as described in WO 06/125437 except to exchanging turmeric with annatto (Annatto: A-320-WS, Chr. Hansen A/S, Boege Alle' 10-12, DK-2970, Hoersholm, Denmark & EMPA221: EMPA, Lerchenfeldstrasse 5, CH-9014, St. Gallen, Switzerland)
Water hardness was adjusted to 15° dH or 6° dH by addition of $CaCl_2$, $MgCl_2$ and $NaHCO_3$ ($Ca^{2+}$:$Mg^{2+}$:$HCO_3$=4:1:7.5 or 2:1:4.5).

TABLE 3

| Composition: Detergent A (wt %) | |
| --- | --- |
| NaOH, pellets (>99%) | 1.05 |
| Linear alkylbenzenesulfonic acid (LAS) (97%) | 7.20 |
| Sodium laureth sulfate (SLES) (28%) | 10.58 |
| Soy fatty acid (>90%) | 2.75 |
| Coco fatty acid (>99%) | 2.75 |
| Alcohol ethoxylate (AEO) with 8 mol EO; Lutensol TO 8 (~100%) | 6.60 |
| Triethanol amine (100%) | 3.33 |
| Na-citrate, dihydrate (100%) | 2.00 |
| DTMPA; diethylenetriaminepentakis(methylene)pentakis(phosphonic acid), heptasodium salt (Dequest 2066 C) (~42% as Na7 salt) | 0.48 |
| MPG (>98%) | 6.00 |
| EtOH, propan-2-ol (90/10%) | 3.00 |
| Glycerol (>99.5%) | 1.71 |
| Sodium formate (>95%) | 1.00 |
| PCA (40% as sodium salt) | 0.46 |
| Water up to | 100 |

TABLE 4

| Composition: Detergent B (wt %) | |
| --- | --- |
| sodium hydroxide (>99%) | 0.50 |
| Linear alkylbenzenesulfonic acid (LAS) (97%) | 5.00 |
| sodium alkyl sulfate (90%) | 5.00 |
| AEOS, sodium (C12) alkyl ether sulfate (70.5%) | 10.00 |
| Coco fatty acid (>99%) | 1.00 |
| Alcohol ethoxylate (AEO) with 7 mol EO (99.5%) | 5.00 |
| MEA, monoethanolamine (99.5%) | 0.20 |
| MPG (>98%) | 3.00 |
| EtOH, propan-2-ol (90/10%) | 1.50 |
| DTPA, diethylenetriaminepentaacetic acid, pentasodium salt, (~40% as Na5 salt) | 0.10 |
| sodium citrate (>99%) | 4.00 |
| sodium formate (>99%) | 1.00 |
| Water up to | 100 |

After washing the textiles were flushed in tap water and excess water was removed from the textiles using filter paper and immediately thereafter the textiles were dried at 100° C. for 15 minutes.

The wash performance was measured as the color change of the washed soiled textile. The soil was cream mixed with annatto. Annatto contains the colorant norbixin, which functions as a pH indicator with a pH dependent color change. Lipase activity leads to release of free fatty acids from the cream acylglycerols and this leads to pH decrease and thereby color change of the norbixin pH indicator. Lipase wash performance can therefore be expressed as the extent of color change of light reflected-emitted from the washed soiled textile when illuminated with white light.

Color measurements were made with a professional flatbed scanner (EPSON EXPRESSION 11000XL, Atea A/S, Lautrupvang 6, 2750 Ballerup, Denmark), which was used to capture an image of the washed soiled textile. To extract a value for the light intensity from the scanned images, 24-bit pixel values from the image were converted into values for red, green and blue (RGB).

Color change due to lipase activity was measured as the change in the reflection-emitting of green light (G) relative to the light intensity value (Int) calculated as:

$$Int = \sqrt{R^2 + G^2 + B^2}$$

The relative wash performance (RP(Wash)) of a lipase relative to a reference lipase was calculated as:

$$RP(\text{Wash}) = (G/Int(\text{tested lipase}) - G/Int(no\ \text{enzyme})) / (G/Int(\text{lipase ref.}) - G/Int(no\ \text{enzyme})).$$

A lipase is considered to exhibit improved wash performance, if it performs better than the reference (RP(Wash) >1). In the context of the present invention the reference enzyme is a lipase shown as SEQ ID NO: 2.

Odor Detection by Solid Phase Micro Extraction Gas Chromatograph Measurements.

The butyric acid release (odor) from the lipase washed swatches were measured by Solid Phase Micro Extraction Gas Chromatography (SPME-GC) using the following method. Cream Annatto stained EMPA221 cotton textile was washed as specified above and after wash, excess water was removed from the textile using filter paper and the textile was thereafter dried at 25° C. for 2 hours. Each SPME-GC measurement was performed with four pieces of the washed and dried textile (5 mm in diameter), which were transferred to a Gas Chromatograph (GC) vial and the vial was closed. The samples were incubated at 30° C. for 24 hours and subsequently heated to 140° C. for 30 minutes and stored at 20° C.-25° C. for at least 4 hours before analysis. The analyses were performed on a Varian 3800 GC equipped with a Stabilwax-DA w/lntegra-Guard column (30 m, 0.32 mm ID and 0.25 micro-m df) and a Carboxen PDMS SPME fiber (85 micro-m). Sampling from each GC vial was done at 50° C. for 8 minutes with the SPME fiber in the headspace over the textile pieces and the sampled compounds were subsequently injected onto the column (injector temperature=250° C.). Column flow=2 ml helium/minute. Column oven temperature gradient: 0 minute=50° C., 2 minutes=50° C., 6 minutes 45 seconds=240° C., 11 minutes 45 seconds=240° C. Detection was done using a Flame Ionization Detector (FID) and the retention time for butyric acid was identified using an authentic standard.

The relative odor release (RP(Odor)) of a lipase is the ratio between the amount butyric acid released (peak area) from a lipase washed swatch and the amount butyric acid released (peak area) from a reference lipase washed swatch, after both values have been corrected for the amount of butyric acid released (peak area) from a non-lipase washed swatch (blank). The relative odor performance (RP(Odor)) is calculated in accordance with the below formula:

RP(Odor)=(odor(tested lipase)−odor(no enzyme))/ (odor(lipase ref.)−odor(no enzyme))

Where odor is the measured butyric acid (peak area) released from the textile surface.

Benefit Risk Factor (RP(Wash)/RP(Odor)).

The Benefit Risk factor (BRF) describing the wash performance (Benefit) compared to the odor release (Risk) can be defined as RP(Wash)/RP(Odor). If the Benefit Risk factor of a lipase is higher than 1, the lipase has better wash performance relative to the released odor compared to the reference lipase (SEQ ID NO: 2).

| Construct Protein Mutations | AMSA Detergent B RP(6° dH, 0.8 g/L) | AMSA Detergent A RP(6° dH, 3.3 g/L) | AMSA Detergent A RP(15° dH, 3.3 g/L) | AMSA Detergent B RP(6° dH, 0.8 g/L) (odor) |
|---|---|---|---|---|
| SEQ ID NO: 2 | 1.00 | 1.00 | 1.00 | 1.00 |
| T231R + N233R | 5.50 | 2.06 | 4.83 | 11.00 |
| G23S + D27N + F51I + E56R + V60E + R118F + T231R + N233R + P256T | 2.93 | 1.22 | 1.46 | 2.41 |
| G23S + D27N + A40I + F51I + E56R + K98I + N101D + R118F + T231R + N233R + T244E + P256T | 1.05 | 1.38 | 1.26 | 1.78 |
| G23S + D27N + A40I + F51I + E56R + V60K + R118F + T231R + N233R + T244E + P256T | 2.66 | 1.43 | 1.79 | 3.18 |
| G23S + T231R + N233R | 3.73 | 1.65 | 2.68 | 6.63 |
| D27N + T231R + N233R | 3.97 | 1.72 | 4.09 | 5.08 |
| A40I + T231R + N233R | 4.83 | 1.94 | 3.52 | 5.16 |
| F51I + T231R + N233R | 4.82 | 1.94 | 3.80 | 6.45 |
| F51L + T231R + N233R | 4.17 | 1.81 | 3.15 | 6.76 |
| E56R + T231R + N233R | 3.75 | 1.56 | 2.59 | 5.52 |
| D57N + T231R + N233R | 3.90 | 1.37 | 2.46 | 5.42 |
| V60E + T231R + N233R | 1.87 | 1.46 | 1.33 | 5.76 |
| V60K + T231R + N233R | 2.56 | 0.96 | −0.38 | 5.20 |
| K98I + T231R + N233R | 4.80 | 2.05 | 4.56 | 3.99 |
| N101D + T231R + N233R | 4.34 | 2.07 | 3.21 | 4.65 |
| R118F + T231R + N233R | 4.30 | 2.10 | 3.24 | 10.12 |
| G163S + T231R + N233R | 3.30 | 1.61 | 2.06 | 6.60 |
| Y220F + T231R + N233R | 2.76 | 0.93 | 0.42 | 4.36 |
| T231R + N233R + T244E | 2.55 | 1.04 | 0.08 | 5.21 |
| T231R + N233R + P256T | 7.82 | 2.38 | 5.71 | 7.76 |
| E56R + R118F + T231R + N233R | 4.96 | 1.77 | 2.97 | 13.97 |
| R118F + T231R + N233R + P256T | 5.10 | 1.89 | 2.68 | 12.22 |
| A40I + R118F + T231R + N233R | 2.11 | 1.22 | 1.06 | 5.68 |
| F51I + E56R + R118F + T231R + N233R | 2.69 | 1.64 | 0.36 | 7.59 |
| F51L + E56R + R118F + T231R + N233R | 3.32 | 1.67 | 1.52 | 7.46 |
| E56R + D57N + R118F + T231R + N233R | 2.96 | 1.31 | 0.75 | 9.75 |
| E56R + V60K + R118F + T231R + N233R | 3.14 | 1.21 | 1.23 | 13.73 |

Example 7: Protein Thermal Unfolding Analysis (TSA, Thermal Shift Assay)

Protein thermal unfolding of variants of SEQ ID NO: 2 was monitored with Sypro Orange (Invitrogen, S-6650) using a real-time PCR instrument (Applied Biosystems; Step-One-Plus). In a 96-well white PCR-plate, 15 µl sample (purified enzyme diluted in 100 mM EPPS, 0.01% Troton-X-100; pH8.0) was mixed (1:1) with Sypro Orange (Conc.=10×; stock solution from supplier=5000×) in water.

The plate was sealed with an optical PCR seal. The PCR instrument was set at a scan-rate of 76° C. per hour, starting at 25° C. and finishing at 96° C.

Fluorescence was monitored every 20 seconds using in-built LED blue light for excitation and ROX-filter (610 nm, emission). Tm-values were calculated as the maximum value of the first derivative (dF/dK) (Gregory et al., 2009, J. Biomol. Screen. 14: 700).

| Construct Protein Mutations | Tm (° C.) |
|---|---|
| SEQ ID NO: 2 | 72.6 |
| T231R + N233R | 71.5 |
| G23S + D27N + F51I + E56R + V60E + R118F + T231R + N233R + P256T | 77.3 |
| G23S + D27N + A40I + F51I + E56R + K98I + N101D + R118F + T231R + N233R + T244E + P256T | 79.8 |
| G23S + D27N + A40I + F51I + E56R + V60K + R118F + T231R + N233R + T244E + P256T | 80.0 |
| G23S + T231R + N233R | 72.6 |
| D27N + T231R + N233R | 72.4 |
| A40I + T231R + N233R | 74.0 |
| F51I + T231R + N233R | 72.2 |
| F51L + T231R + N233R | 71.9 |
| E56R + T231R + N233R | 72.3 |
| D57N + T231R + N233R | 72.1 |
| V60E + T231R + N233R | 71.1 |
| V60K + T231R + N233R | 71.6 |
| K98I + T231R + N233R | 72.0 |
| N101D + T231R + N233R | 72.3 |
| R118F + T231R + N233R | 72.7 |
| G163S + T231R + N233R | 71.9 |
| Y220F + T231R + N233R | 70.0 |
| T231R + N233R + T244E | 72.3 |
| T231R + N233R + P256T | 75.2 |
| E56R + R118F + T231R + N233R | 73.1 |
| R118F + T231R + N233R + P256T | 75.7 |
| A40I + R118F + T231R + N233R | 74.6 |
| F51I + E56R + R118F + T231R + N233R | 74.2 |
| F51L + E56R + R118F + T231R + N233R | 73.9 |
| E56R + D57N + R118F + T231R + N233R | 72.6 |
| E56R + V60K + R118F + T231R + N233R | 73.1 |

Detergent Examples

Examples 1-5

Unit Dose Laundry detergent compositions. Such unit dose formulations can comprise one or multiple compartments.

| | 1 (wt %) | 2 (wt %) | 3 (wt %) | 4 (wt %) | 5 (wt %) |
|---|---|---|---|---|---|
| Alkylbenzene sulfonic acid | 14.5 | 14.5 | 14.5 | 14.5 | 14.5 |
| C12-18 alkyl ethoxy 3 sulfate | 7.5 | 7.5 | 7.5 | 7.5 | 7.5 |
| C12-18 alkyl 7-ethoxylate | 13.0 | 13.0 | 13.0 | 13.0 | 13.0 |
| Citric Acid | 0.6 | 0.6 | 0.6 | 0.6 | 0.6 |
| Fatty Acid | 14.8 | 14.8 | 14.8 | 14.8 | 14.8 |
| Amylase (mg active) | 6 | 12 | 8 | 0.2 | 0.10 |
| Ethoxylated Polyethylenimine[2] | 4.0 | 4.0 | 4.0 | 4.0 | 4.0 |
| Protease (Purafect Prime ®, 40.6 mg active/g) | 1.4 | 2.0 | 0.9 | 1.2 | 0 |
| Cellulase (Celluclean, active protein) | 0.1 | 0.2 | | | 0.1 |
| Lipase described herein (active protein) | 3.0 | 2.0 | 1.0 | 4.0 | 2.0 |
| Hydroxyethane diphosphonic acid | 1.2 | 1.2 | 1.2 | 1.2 | 1.2 |
| Brightener | 0.3 | 0.3 | 0.3 | 0.3 | 0.3 |
| P-diol | 15.8 | 13.8 | 13.8 | 13.8 | 13.8 |
| Glycerol | 6.1 | 6.1 | 6.1 | 6.1 | 6.1 |
| MEA | 8.0 | 8.0 | 8.0 | 8.0 | 8.0 |
| TIPA | — | — | 2.0 | — | — |
| TEA | — | 2.0 | — | — | — |
| Cumene sulphonate | — | — | — | — | 2.0 |
| cyclohexyl dimethanol | — | — | — | 2.0 | — |
| Water | 10 | 10 | 10 | 10 | 10 |
| Structurant | 0.14 | 0.14 | 0.14 | 0.14 | 0.14 |
| Perfume | 1.9 | 1.9 | 1.9 | 1.9 | 1.9 |
| Buffers (monoethanolamine) | | | To pH 8.0 | | |
| Solvents (1,2 propanediol, ethanol) | | | To 100% | | |

Example 6. Multiple Compartment Unit Dose Compositions

Multiple compartment unit dose laundry detergent formulations of the present invention are provided below. In these examples the unit dose has three compartments, but similar compositions can be made with two, four or five compartments. The film used to encapsulate the compartments is polyvinyl alcohol.

| Base composition | 6 (wt %) | 7 (wt %) |
|---|---|---|
| Glycerol (min 99) | 5.3 | 4.0 |
| 1,2-propanediol | 10.0 | 11.2 |
| Dipropylene glycol | — | 4.1 |
| Citric Acid | 0.5 | 0.8 |
| Monoethanolamine | 10.0 | 10.8 |
| Caustic soda | — | |
| Dequest 2010 | 1.1 | 1.1 |
| Potassium sulfite | 0.2 | 0.2 |
| Lipase variant (mg active) | 8.0 | 8.0 |
| Nonionic Marlipal C24EO7 | 20.1 | 3.9 |
| HLAS | 24.6 | 22.8 |
| HAE3S (C24AE3S) anionic surfactant | — | 15.6 |
| Optical brightener FWA49 | 0.2 | 0.35 |
| C12-15 Fatty acid | 16.4 | 6.3 |
| HEDP chelant | — | 2.4 |
| Polymer Lutensit Z96 | 2.9 | |
| Polyethyleneimine ethoxylate PEI600 E20 | 1.1 | 3.4 |
| Hueing Dye (polymeric) | — | 0.04 |
| Amphiphilic graft polymer | | |
| Texcare SRA300 | | |
| CMC | | |
| MgCl2 | 0.2 | 0.2 |
| Solvents (1,2 propanediol, ethanol, water) | To 100% | To 100% |

| | Multi-compartment formulations | | | | | |
|---|---|---|---|---|---|---|
| | Composition | | | | | |
| | 1 | | | 2 | | |
| Compartment | A | B | C | A | B | C |
| Volume of each compartment | 40 ml | 5 ml | 5 ml | 40 ml | 5 ml | 5 ml |
| Active material in Wt. % | | | | | | |
| Perfume | 1.6 | 1.6 | 1.6 | 1.6 | 1.6 | 1.6 |
| Dyes | <0.01 | <0.01 | <0.01 | <0.01 | <0.01 | <0.01 |
| TiO2 | 0.1 | — | — | — | 0.1 | — |
| Sodium Sulfite | 0.4 | 0.4 | 0.4 | 0.3 | 0.3 | 0.3 |
| Acusol 305 | 1.2 | 2 | | | | |
| Hydrogenated castor oil | 0.14 | 0.14 | 0.14 | 0.14 | 0.14 | 0.14 |
| Base Composition 1 | Add to 100% | Add to 100% | Add to 100% | Add to 100% | Add to 100% | Add to 100% |

Raw Materials and Notes for Detergent Examples 1-7

Linear alkylbenzenesulfonate having an average aliphatic carbon chain length C11-C18
C12-18 Dimethylhydroxyethyl ammonium chloride
AE3S is C12-15 alkyl ethoxy (3) sulfate
AE7 is C12-15 alcohol ethoxylate, with an average degree of ethoxylation of 7
AE9 is C12-16 alcohol ethoxylate, with an average degree of ethoxylation of 9
HSAS is a mid-branched primary alkyl sulfate with carbon chain length of about 16-17 as disclosed in U.S. Pat. Nos. 6,020,303 and 6,060,443
Polyacrylate MW 4500 is supplied by BASF
Carboxymethyl cellulose is Finnfix® V supplied by CP Kelco, Arnhem, Netherlands
CHEC is a cationically modified hydroxyethyl cellulose polymer.
Phosphonate chelants are, for example, diethylenetetraamine pentaacetic acid (DTPA)
Hydroxyethane di phosphonate (HEDP)
S-ACMC is carboxymethylcellulose conjugated with C.I. Reactive Blue 19product name AZO-CM-CELLULOSE
Soil release agent is Repel-o-tex® PF
Acrylic Acid/Maleic Acid Copolymer is molecular weight 70,000 and acrylate:maleate ratio 70:30
Hueing Dye is Liquitint® Violet CT polymeric hueing dye, supplied by Milliken, Spartanburg, S.C., USA
Amphiphilic graft Random graft copolymer is a polyvinyl acetate grafted polyethylene oxide copolymer having a polyethylene oxide backbone and multiple polyvinyl acetate side chains. The molecular weight of the polyethylene oxide backbone is about 6000 and the weight ratio of the polyethylene oxide to polyvinyl acetate is about 40 to 60 and no more than 1 grafting point per 50 ethylene oxide units.
[2] Polyethyleneimine (MW=600) with 20 ethoxylate groups per —NH.
[3] Amphiphilic alkoxylated polymer is a polyethylenimine (MW 600), prepared from a polymer that is derivatised to contain 24 ethoxylate groups per —NH and 16 Propoxylate groups per —NH.
[4] lipase and amylase are shown as mgs of active enzyme per 100 g of detergent.
[a] Proxel GXL, 20% aqueous dipropylene glycol solution of 1,2-benzisothiazolin-3-one, supplied by Lonza.
[b] N,N-bis(hydroxyethyl)-N,N-dimethyl ammonium chloride fatty acid ester. The iodine value of the parent fatty acid of this material is between 18 and 22. The material as obtained from Evonik contains impurities in the form of free fatty acid, the monoester form of N,N-bis(hydroxyethyl)-N,N-dimethyl ammonium chloride fatty acid ester, and fatty acid esters of N,N-bis(hydroxyethyl)-N-methylamine.
[c] MP10®, supplied by Dow Corning, 8% activity
[d] as described in U.S. Pat. No. 8,765,659, expressed as 100% encapsulated perfume oil
[e] Rheovis® CDE, cationic polymeric thickener supplied by BASF
[f] N,N-dimethyl octanamide and N,N-dimethyl decanamide in about a 55:45 weight ratio, tradename Steposol® M-8-10 from the Stepan Company The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A water-soluble unit dose article comprising a water-soluble film and a liquid laundry detergent composition, wherein the liquid laundry detergent composition comprises:
   a variant lipase having an amino acid sequence that is at least 90% identical to the amino acid sequence of SEQ ID NO: 2 with the exception of a substitution at a position corresponding to the amino acid at position 118 of the amino acid sequence of SEQ ID NO: 2, and comprises
   (i) a substitution at one or more positions corresponding to the amino acids at positions 40, 244, or 60 of the amino acid sequence of SEQ ID NO: 2 and (ii) the substitutions to T231R and N233R; wherein said variant lipase has lipase activity;
   and a detergent adduct.

2. The water-soluble unit dose article of claim 1, wherein said variant lipase comprises a substitution at a position corresponding to the amino acid at position 40 of the amino acid sequence of SEQ ID NO: 2.

3. The water-soluble unit dose article of claim 1, comprising the substitutions A40I and R118F.

4. The water-soluble unit dose article of claim 1, wherein said variant lipase comprises the substitution R118F and one or more of the substitutions G23S, D27N, A40I, F51I,L, E56R, D57N, K98I, N101D, G163S, Y220F, T244E, and P256T.

5. The water-soluble unit dose article of claim 1:
   wherein the variant lipase comprises the substitutions R118F+T231R+N233R and one or more of the substitutions to G23S, D27N, A40I, F51I,L, E56R, D57N, K98I, N101D, G163S, Y220F, T244E, and P256T; or
   wherein the variant lipase comprises the substitutions E56R+R118F+T231R+N233R and one or more of the substitutions G23S, D27N, A40I, F51I,L, D57N, K98I, N101D, G163S, Y220F, T244E, and P256T; or
   wherein the variant lipase comprises the substitutions F51I,L+E56R+R118F+T231R+N233R and one or more of the substitutions G23S, D27N, A40I, D57N, K98I, N101D, G163S, Y220F, T244E, and P256T; or
   wherein the variant lipase comprises the substitutions E56R+R118F+T231R+N233R+P256T and one or more of the substitutions G23S, D27N, A40I, F51I,L, D57N, V60E,K, K98I, N101D, G163S, Y220F, and T244E; or
   wherein the variant lipase comprises the substitutions F51I,L+E56R+R118F+T231R+N233R+P256T and one or more of the substitutions G23S, D27N, A40I, D57N, K98I, N101D, G163S, Y220F, and T244E;
   wherein the variant lipase comprises the substitutions G23S+F51I,L+E56R+R118F+T231R+N233R and one or more of the substitutions D27N, A40I, D57N, K98I, N101D, G163S, Y220F, T244E, and P256T.

6. The water-soluble unit dose article of claim 1, wherein the variant lipase further comprises the substitution P256T.

7. The water-soluble unit dose article of claim 1, wherein one or more variant lipase is encapsulated in a microcapsule, wherein the membrane of the microcapsule is produced by cross-linking of a polybranched polyamine having a molecular weight of more than 1 kDa.

8. The water-soluble unit dose article of claim 1, wherein the liquid laundry detergent composition comprises a polymer selected from carboxymethyl cellulose, a hydrophobically modified carboxymethyl cellulose or a mixture thereof.

9. The water-soluble unit dose article of claim 1, wherein the liquid laundry detergent composition comprises a non-soap anionic surfactant comprises linear alkylbenzene sulphonate, alkoxylated alkyl sulphate or a mixture thereof.

10. The water-soluble unit dose article of claim 1, wherein the liquid laundry detergent composition comprises:
    a. a cationic polysaccharide selected from cationically modified hydroxyethyl cellulose, cationically modified hydroxypropyl cellulose, cationically and hydrophobically modified hydroxyethyl cellulose, cationically and hydrophobically modified hydroxypropyl cellulose, or a mixture thereof;
    b. an alkoxylated polyethyleneimine;
    c. a mixture thereof.

11. A process for washing fabrics comprising the steps of:
    a. combining the water-soluble unit dose article of claim 1 with sufficient water to dissolve the water-soluble film and dilute the laundry detergent composition to form a wash liquor;
    b. contacting the wash liquor with at least one fabric to be washed.

12. The water-soluble unit dose article of claim 1, wherein the variant lipase further comprises a substitution at a position corresponding to the amino acid at position 23 of the amino acid sequence of SEQ ID NO: 2.

* * * * *